United States Patent
Ravensbergen et al.

(10) Patent No.: US 10,599,047 B2
(45) Date of Patent: Mar. 24, 2020

(54) METROLOGY APPARATUS, LITHOGRAPHIC SYSTEM, AND METHOD OF MEASURING A STRUCTURE

(71) Applicant: ASML Netherlands B.V., Veldhoven (NL)

(72) Inventors: Janneke Ravensbergen, Eindhoven (NL); Nitesh Pandey, Eindhoven (NL); Zili Zhou, Eindhoven (NL); Armand Eugene Albert Koolen, Nuth (NL); Sebastianus Adrianus Goorden, Eindhoven (NL); Bastiaan Onne Fagginger Auer, Eindhoven (NL); Simon Gijsbert Josephus Mathijssen, Rosmalen (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/988,677

(22) Filed: May 24, 2018

(65) Prior Publication Data
US 2018/0348645 A1    Dec. 6, 2018

(30) Foreign Application Priority Data

Jun. 2, 2017 (EP) .................................. 17174269
Jun. 26, 2017 (EP) .................................. 17177960
Nov. 6, 2017 (EP) .................................. 17200068

(51) Int. Cl.
*G03F 7/20* (2006.01)
*G01N 21/95* (2006.01)
(Continued)

(52) U.S. Cl.
CPC .......... *G03F 7/7055* (2013.01); *G01B 11/272* (2013.01); *G01N 21/4788* (2013.01);
(Continued)

(58) Field of Classification Search
CPC ...................................... G03F 7/70633–70683
See application file for complete search history.

(56) References Cited

U.S. PATENT DOCUMENTS 5,048,926 A * 9/1991 Tanimoto ............ G03F 7/70208
359/485.07
6,469,793 B1 10/2002 Stanton
(Continued)

FOREIGN PATENT DOCUMENTS

CN 102089616 B 6/2011
TW I578113 B 4/2017
(Continued)

OTHER PUBLICATIONS

International Search Report and Written Opinion of the International Searching Authority directed to related International Patent Application No. PCT/EP2018/062547, dated Jun. 22, 2018; 9 pages.

*Primary Examiner* — Shawn Decenzo
(74) *Attorney, Agent, or Firm* — Sterne, Kessler, Goldstein & Fox P.L.L.C.

(57) ABSTRACT

A metrology apparatus is disclosed that measures a structure formed on a substrate to determine a parameter of interest. The apparatus comprises an optical system configured to focus radiation onto the structure and direct radiation after reflection from the structure onto a detector, wherein: the optical system is configured such that the detector detects a radiation intensity resulting from interference between radiation from at least two different points in a pupil plane field distribution, wherein the interference is such that a component of the detected radiation intensity containing information about the parameter of interest is enhanced relative to one or more other components of the detected radiation intensity.

15 Claims, 14 Drawing Sheets

(51) Int. Cl.
  *G01N 21/956* (2006.01)
  *G01N 21/47* (2006.01)
  *G01B 11/27* (2006.01)

(52) U.S. Cl.
  CPC ... *G01N 21/9501* (2013.01); *G01N 21/95623* (2013.01); *G03F 7/70625* (2013.01); *G03F 7/70633* (2013.01)

(56) References Cited

U.S. PATENT DOCUMENTS

| | | | |
|---|---|---|---|
| 6,549,267 B1 * | 4/2003 | Kudo | G03B 27/42 355/53 |
| 6,795,168 B2 * | 9/2004 | Wang | G03F 7/70208 355/53 |
| 6,795,198 B1 | 9/2004 | Fuchs et al. | |
| 7,561,282 B1 | 7/2009 | Widmann | |
| 9,164,397 B2 * | 10/2015 | Manassen | G01N 21/55 |
| 10,162,271 B2 | 12/2018 | Smilde et al. | |
| 2008/0266561 A1 * | 10/2008 | Kandel | G01B 11/272 356/399 |
| 2011/0032535 A1 | 2/2011 | Liesener et al. | |
| 2013/0044331 A1 | 2/2013 | Manassen et al. | |
| 2018/0188663 A1 * | 7/2018 | Levinski | G03F 7/70625 |
| 2019/0113852 A1 * | 4/2019 | Ravensbergen | G03F 7/70633 |

FOREIGN PATENT DOCUMENTS

| | | |
|---|---|---|
| TW | I582548 B | 5/2017 |
| WO | WO 2009/149103 A1 | 12/2009 |
| WO | WO 2016/096310 A1 | 6/2016 |

* cited by examiner

Fig. 3
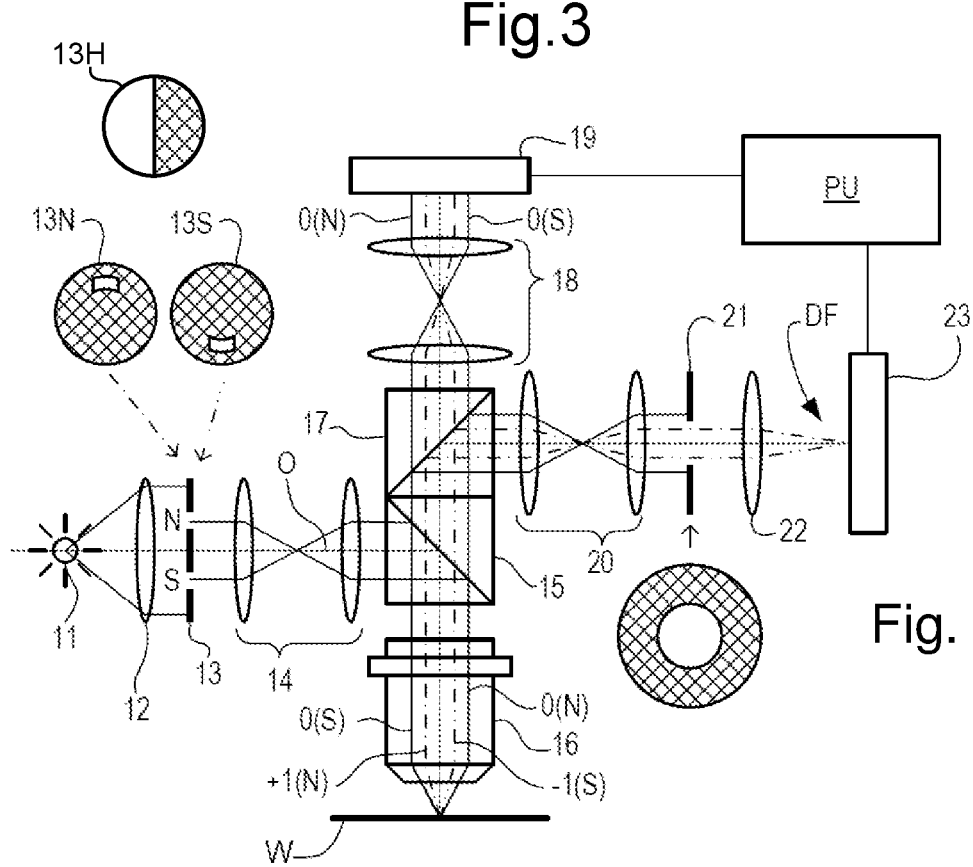
Fig. 3(a)
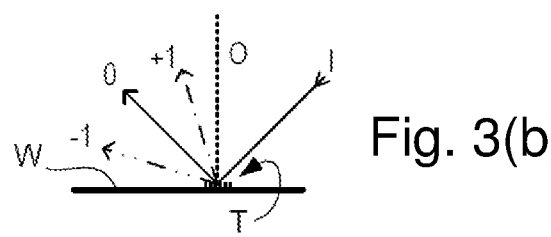
Fig. 3(b)
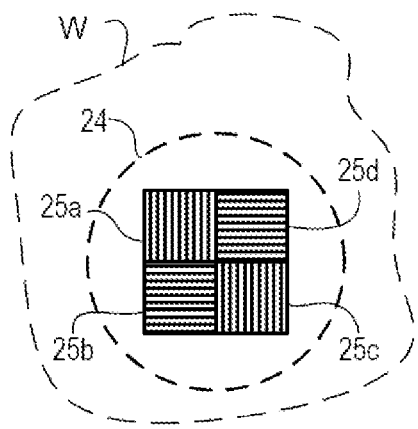
Fig. 3(c)
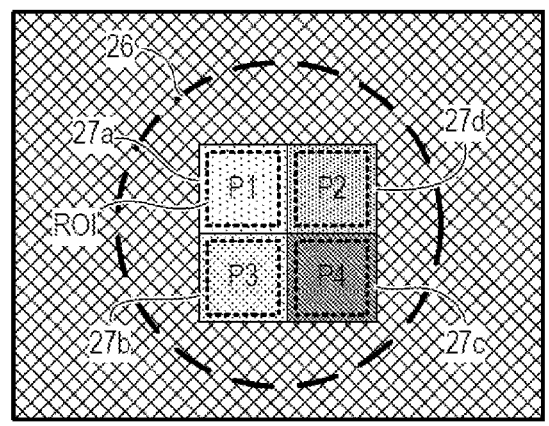
Fig. 3(d)

METROLOGY APPARATUS, LITHOGRAPHIC SYSTEM, AND METHOD OF MEASURING A STRUCTURE

FIELD

The present invention relates to a metrology apparatus for measuring a structure formed on a substrate by a lithographic process, a lithographic system, and a method of measuring a structure formed on a substrate by a lithographic process.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

In a known metrology technique, overlay measurement results are obtained by measuring an overlay target twice under certain conditions, while either rotating the overlay target or changing the illumination mode or imaging mode to obtain separately the $-1^{st}$ and the $+1^{st}$ diffraction order intensities. The intensity asymmetry, a comparison of these diffraction order intensities, for a given overlay target provides a measurement of target asymmetry; that is, asymmetry in the target. This asymmetry in the overlay target can be used as an indicator of overlay (undesired misalignment of two layers).

Measurement of overlay (or other asymmetries in target structures) using the above metrology technique is difficult where the structures concerned are at the resolution of device features to be manufactured. This is because high resolution features cause correspondingly high angles of diffraction, which are difficult to capture, or diffraction orders become evanescent (non-propagating). For structures defined by layers that are very close to each other, such as may be the case after etching has been carried out, it may still be possible to obtain some information about asymmetry from zeroth order scattering. However, it is difficult to obtain adequate sensitivity in such measurements, particularly where the layer separation is not very small.

SUMMARY

It is desirable to improve measurement of target asymmetry or other parameters of interest, particularly for high resolution targets.

According to an aspect of the invention, there is provided a metrology apparatus for measuring a structure formed on a substrate to determine a parameter of interest, the metrology apparatus comprising: an optical system configured to focus radiation onto the structure and direct radiation after reflection from the structure onto a detector, wherein: the optical system is configured such that the detector detects a radiation intensity resulting from interference between radiation from at least two different points in a pupil plane field distribution, wherein the interference is such that a component of the detected radiation intensity containing information about the parameter of interest is enhanced relative to one or more other components of the detected radiation intensity.

According to an aspect of the invention, there is provided a method of measuring a structure formed on a substrate to determine a parameter of interest, the method comprising: focusing radiation onto the structure and using a detector to detect radiation after reflection from the structure, wherein: the detector detects a radiation intensity resulting from interference between radiation from at least two different points in a pupil plane field distribution, wherein the interference is such that a component of the detected radiation intensity containing information about the parameter of interest is enhanced relative to one or more other components of the detected radiation intensity.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIGS. 3(a)-3(d) comprise FIG. 3(a) a schematic diagram of a dark field scatterometer for use in measuring targets using a first pair of illumination apertures; FIG. 3(b) a detail of diffraction spectrum of a target grating for a given direction of illumination; FIG. 3(c) a depiction of a known form of multiple grating target and an outline of a measurement spot on a substrate; and FIG. 3(d) a depiction of an image of the target of FIG. 3(c) obtained in the scatterometer of FIG. 3(a)

DETAILED DESCRIPTION OF EXEMPLARY EMBODIMENTS

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the present invention may be implemented.

Figure 1:
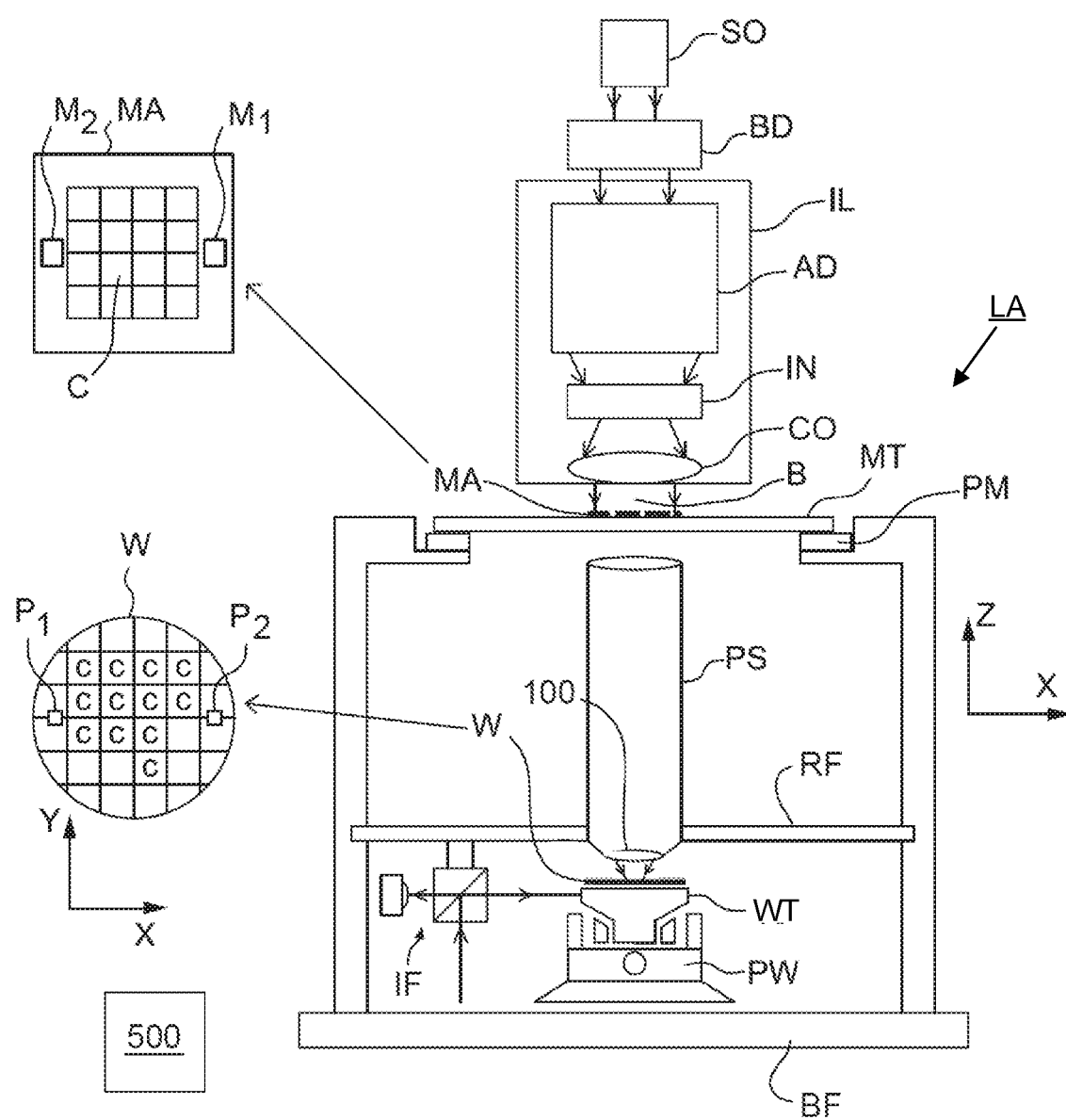
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist coated wafer) W and connected to a second positioner PW configured to accurately position the substrate in accordance with certain parameters, and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic, or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing various types of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

In this embodiment, for example, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables and, for example, two or more mask tables. In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (which are commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
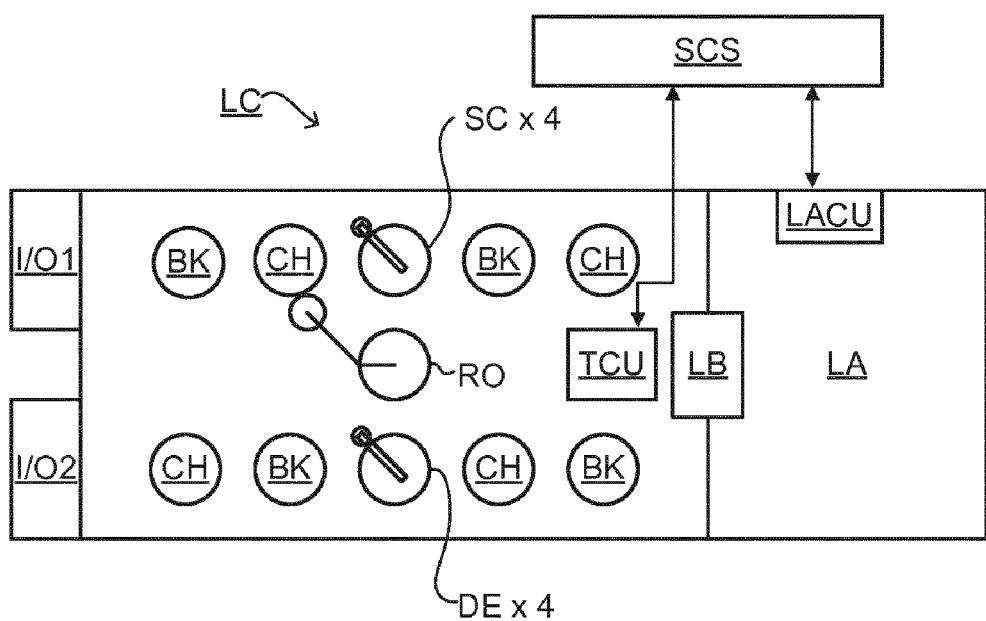
FIG. 2 depicts a lithographic cell or cluster.

As shown in FIG. 2 the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU that is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments, for example, can be made to exposures of subsequent substrates, especially if the inspection can be done soon and fast enough that other substrates of the same batch are still to be exposed. Also, already exposed substrates may be stripped and reworked to improve yield, or possibly be discarded, thereby avoiding performing exposures on substrates that are known to be faulty. In a case where only some target portions of a substrate are faulty, further exposures can be performed only on those target portions that are deemed to be non-faulty.

A metrology apparatus is used to determine the properties of the substrates, and in particular, how the properties of different substrates or different layers of the same substrate vary from layer to layer. The metrology apparatus may be integrated into the lithographic apparatus LA or the lithocell LC or may be a stand-alone device. To enable most rapid measurements, it is desirable that the metrology apparatus measure properties in the exposed resist layer immediately after the exposure. However, the latent image in the resist has a very low contrast, as in there is only a very small difference in refractive index between the parts of the resist which have been exposed to radiation and those which have not—and not all metrology apparatus have sufficient sensitivity to make useful measurements of the latent image. Therefore measurements may be taken after the post-exposure bake step (PEB) that is customarily the first step carried out on exposed substrates and increases the contrast between exposed and unexposed parts of the resist. At this stage, the image in the resist may be referred to as semi-latent. It is also possible to make measurements of the developed resist image, at which point either the exposed or unexposed parts of the resist have been removed, or after a pattern transfer step such as etching. The latter possibility limits the possibilities for rework of faulty substrates but may still provide useful information.

A metrology apparatus is shown in FIG. 3(a). A target T and diffracted rays of measurement radiation used to illuminate the target are illustrated in more detail in FIG. 3(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the examples of FIG. 3 forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. The rest of the pupil plane is desirably dark as any unnecessary light outside the desired illumination mode will interfere with the desired measurement signals. In other embodiments, as discussed below with reference to FIGS. 4-8, aperture plates 13 of different form may be used, such as the aperture plate labeled 13H.

As shown in FIG. 3(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line +1 and double dot-chain line −1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

In the example of FIG. 3 at least the 0 and +1 orders diffracted by the target T on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, $2^{nd}$, $3^{rd}$ and higher order beams (not shown in FIG. 3) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented.

FIG. 3(c) depicts a (composite) target formed on a substrate according to known practice. The target in this example comprises four gratings 25a to 25d positioned closely together so that they will all be within a measurement scene or measurement spot 24 formed by the metrology radiation illumination beam of the metrology apparatus. The four gratings thus are all simultaneously illuminated and simultaneously imaged on sensors 19 and 23. In an example dedicated to measurement of overlay, gratings 25a to 25d are themselves composite gratings formed by overlying gratings that are patterned in different layers of the semi-conductor device formed on substrate W. Gratings 25a to 25d may have differently biased overlay offsets (deliberate mismatch between layers) in order to facilitate measurement of overlay between the layers in which the different parts of the composite gratings are formed. Such techniques are well known to the skilled person and will not be described further. Gratings 25a to 25d may also differ in their orientation, as shown, so as to diffract incoming radiation in X and Y directions. In one example, gratings 25a and 25c are X-direction gratings with biases of the +d, −d, respectively. Gratings 25b and 25d are Y-direction gratings with offsets +d and −d respectively. Separate images of these gratings can be identified in the image captured by sensor 23. This is only one example of a target. A target may comprise more or fewer than four gratings, or only a single grating.

FIG. 3(d) shows an example of an image that may be formed on and detected by the sensor 23, using the target of FIG. 3(c) in the apparatus of FIG. 3(a). While the pupil plane image sensor 19 cannot resolve the different individual gratings 25a to 25d, the image sensor 23 can do so. The dark rectangle represents the field of the image on the sensor, within which the illuminated spot 24 on the substrate is imaged into a corresponding circular area 26. Within this, rectangular areas 27a to 27d represent the images of the small target gratings 25a to 25d. If the targets are located in product areas, product features may also be visible in the periphery of this image field. Image processor and controller PU processes these images using pattern recognition to identify the separate images 27a to 27d of gratings 25a to 25d. In this way, the images do not have to be aligned very precisely at a specific location within the sensor frame, which greatly improves throughput of the measuring apparatus as a whole.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

As mentioned in the introductory part of the description, measurements of overlay and other asymmetries in target structures is difficult when structures are at the resolution of device features to be manufactured. This is because it is difficult to capture higher than zeroth order diffracted radiation. In an arrangement of the type depicted in FIGS. 3(a)-(d) for example, the angles of reflection of either or both of the +1 and −1 diffracted orders become too high for both to be captured by the objective lens 16 or these orders become evanescent (non-propagating).

The inventors have recognized that target asymmetry makes a contribution, albeit extremely small, to zeroth order reflected beams (i.e. specular reflected beams). Zeroth order reflected beams are relatively easily captured by the objective lens 16. The inventors have further recognized that novel interferometry can be used to measure the asymmetry contribution to the zeroth order reflected beams with high sensitivity, as well as other parameters of interest. Embodiments based on this principle are described below with reference to FIGS. 4-20.

According to an embodiment, a metrology apparatus for measuring a structure formed on a substrate by a lithographic process is provided. In an embodiment, the metrology apparatus is broadly similar to the metrology apparatus of FIG. 3 in the case where only the first measurement branch (in which a detector is placed in a pupil plane) is provided. It is not however necessary for the detection to take place in the pupil plane. In other embodiments the detector is placed in the image plane or in a plane between the image plane and the pupil plane. The metrology apparatus comprises an optical system (described below with reference to FIGS. 4 and 5) that focuses radiation onto the structure and directs radiation after reflection to a detector 38. The optical system is configured such that the detector 38 detects a radiation intensity resulting from interference between radiation from at least two different points in a pupil plane field distribution. The interference is such that a component of the detected radiation intensity containing information about a parameter of interest is enhanced relative to one or more other components of the detected radiation intensity (due to at least partially destructive interference of radiation corresponding to the one or more other components). The optical system introduces the required spatial coherence between different points in the pupil plane field distribution, so the functionality can be implemented using an incoherent radiation source. In an embodiment, the detected radiation intensity results from zeroth order reflection from the structure. The approach is therefore suitable for measuring high resolution features (e.g. features at the resolution of device structures to be manufactured).

The embodiments discussed with reference to FIGS. 4-9 implement the above functionality using a form of common path interferometry, in which light that is split by a beam splitter follows a common path in different senses before being interfered after passing through the beam splitter a second time. The parameter of interest in these embodiments is overlay, but the principle could be applied to other parameters of interest.

Figure 4:
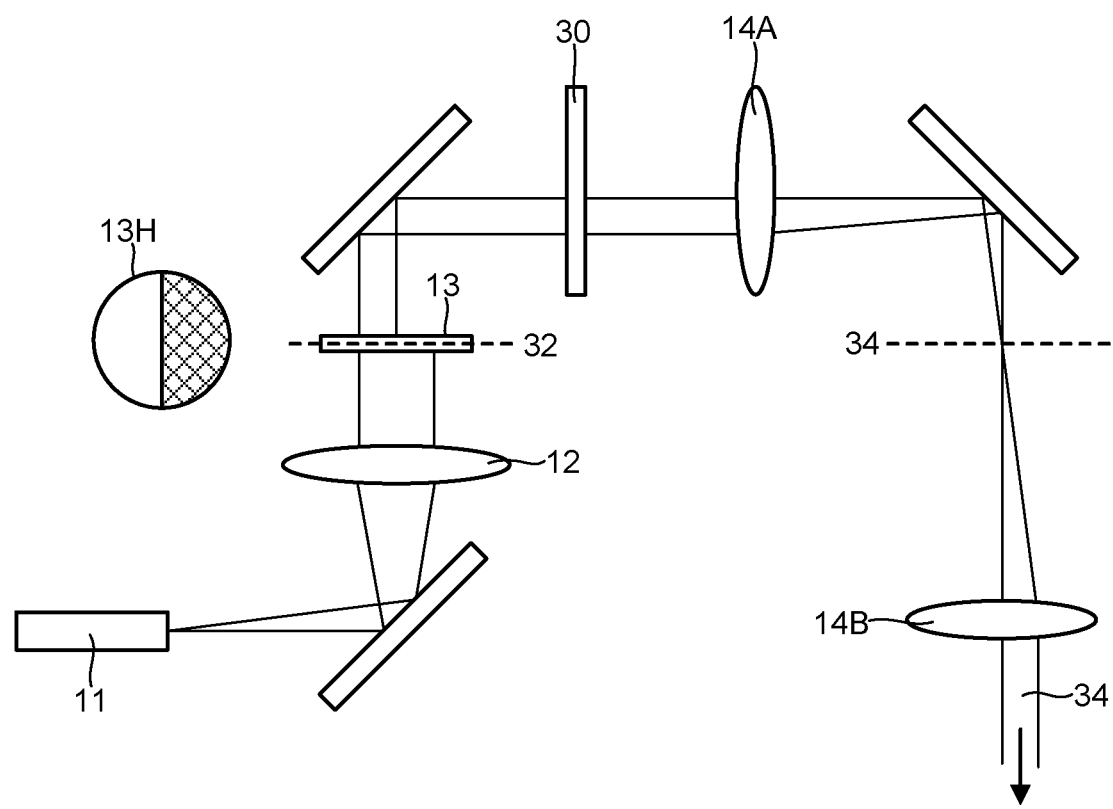
FIG. 4 depicts optical elements of a metrology apparatus that provide an input radiation beam to an optical unit comprising a beam splitter.
Figure 5:
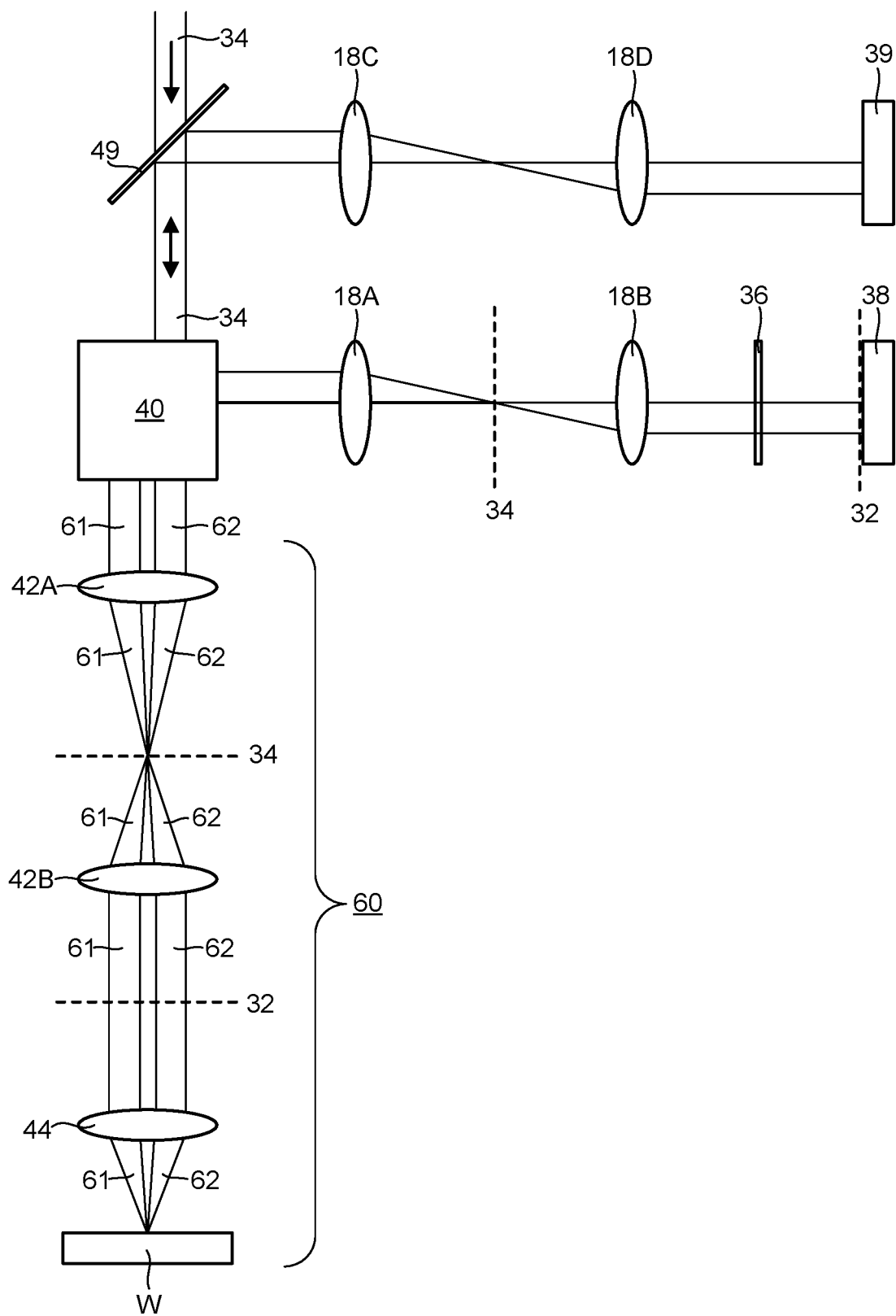
FIG. 5 depicts the optical unit configured to receive the input radiation beam from the arrangement of FIG. 4 and an optical system for directing first and second radiation beams onto a substrate and directing reflected first and second radiation beams onto a detector.
Figure 6:
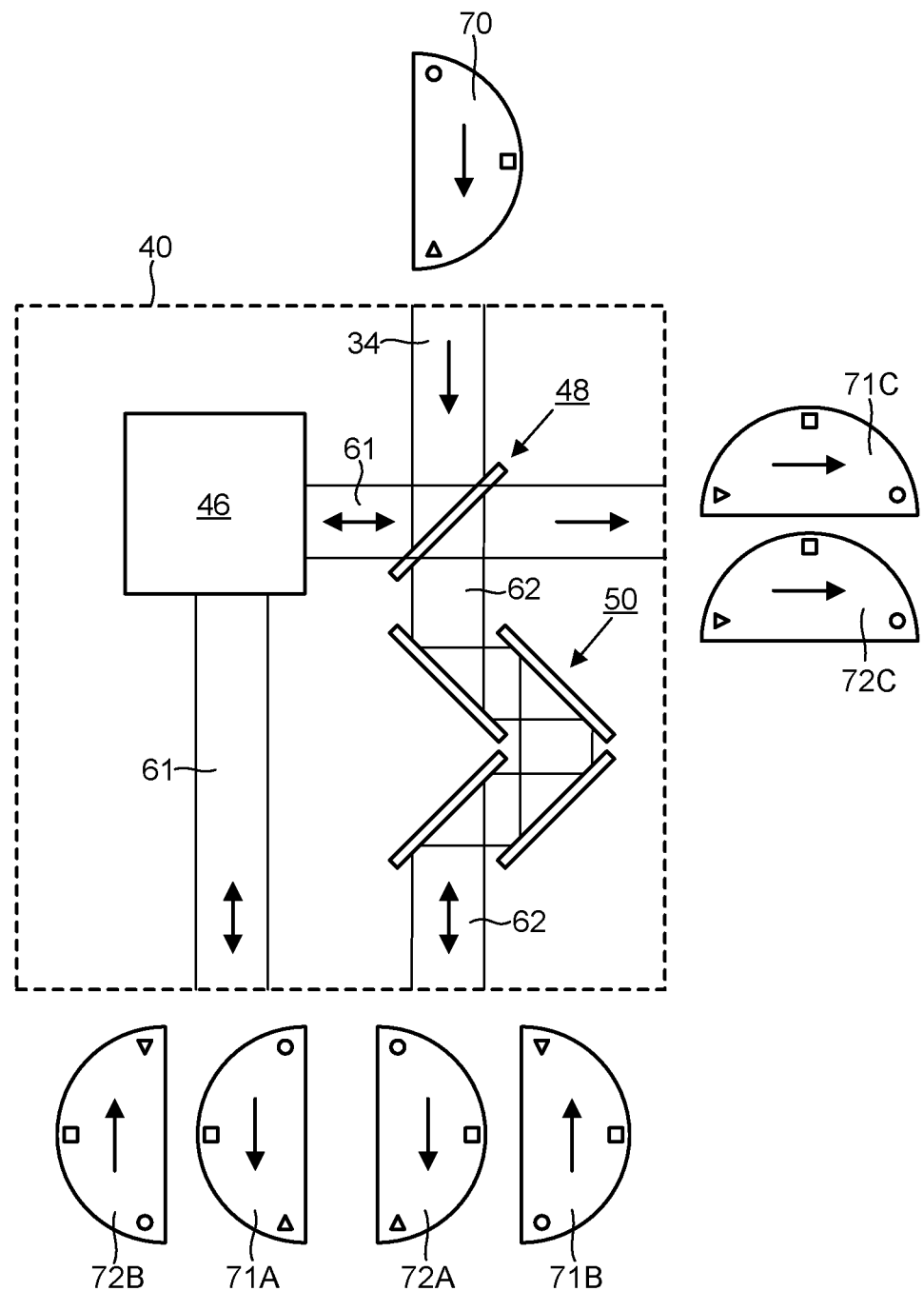
FIG. 6 depicts operation of an optical unit of the arrangement of FIG. 5 in further detail, showing pupil plane field distributions in radiation beams propagating to and from the beam splitter.
Figure 7:
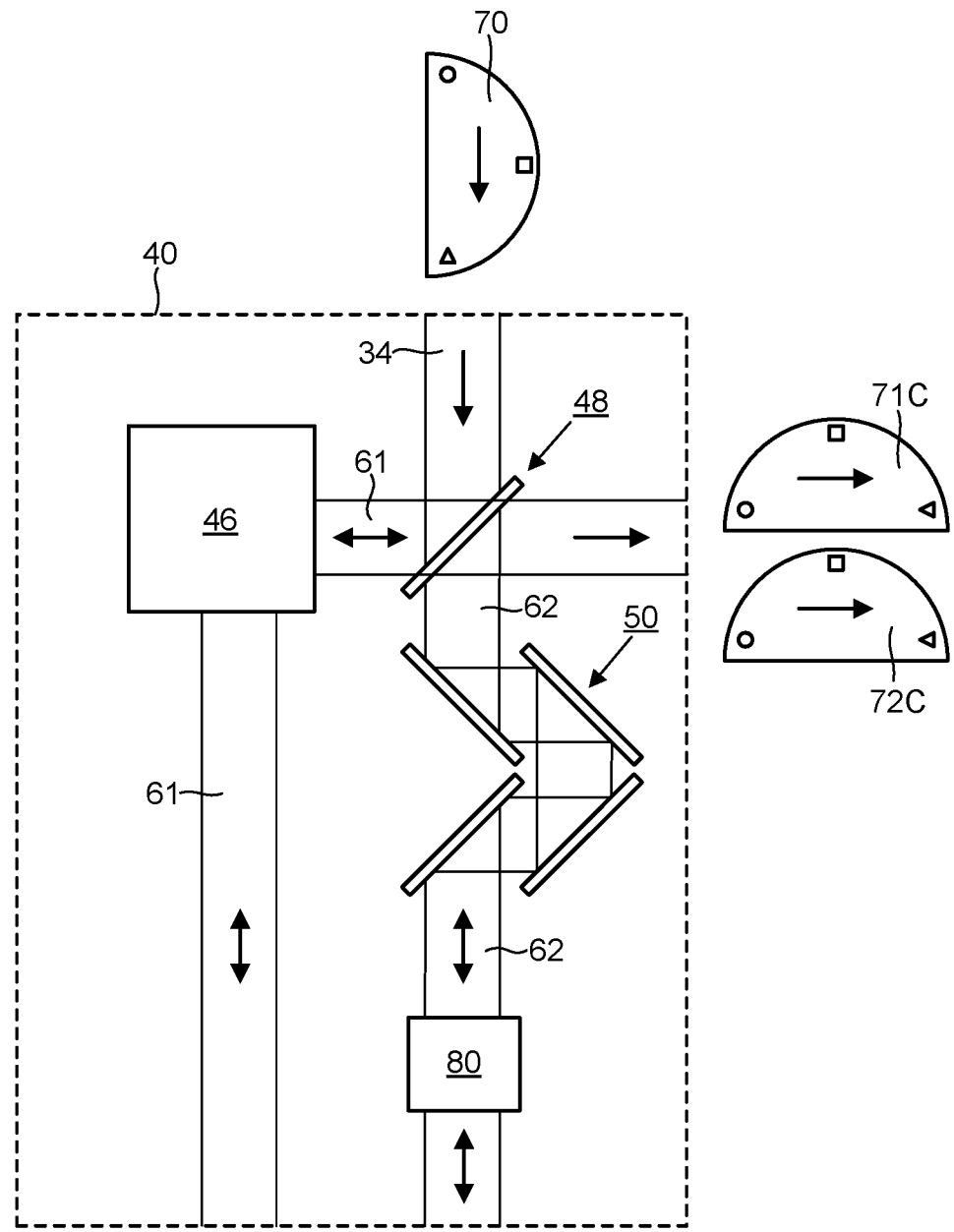
FIG. 7 depicts operation of an alternative optical unit based on the optical unit of FIG. 6 with an additional flip being performed in the second branch.
Figure 8:
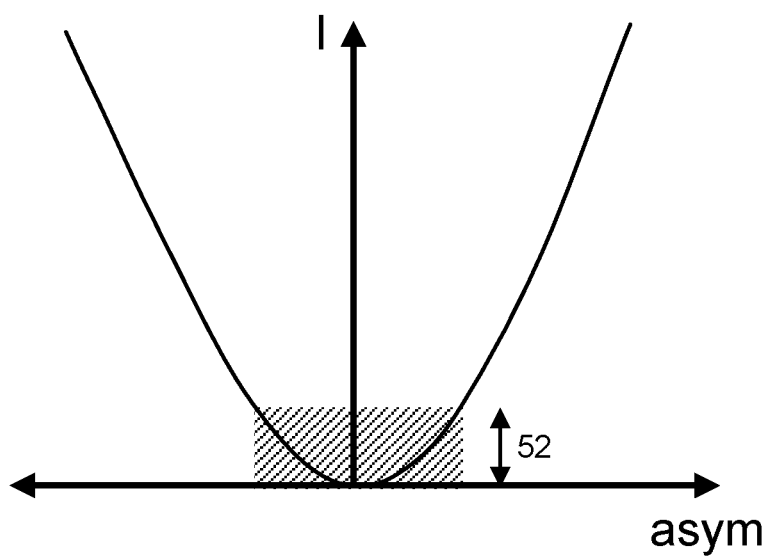
FIG. 8 is a graph depicting a typical variation of signal intensity I with target asymmetry for an unbiased target.

FIG. 4 depicts optical elements of the metrology apparatus for providing an input radiation beam 34 to an optical unit 40 (shown in FIGS. 5-7). A source 11 (e.g. an output end of an optical fiber) provides a radiation beam that is passed through a lens system comprising lenses 12, 14A and 14B. The lenses 12, 14A and 14B correspond to lenses 12 and 14 shown in FIG. 3. Like the lenses 12 and 14 of FIG. 3, the lenses 12, 14A and 14B may be arranged in a double sequence of a 4F arrangement. A pupil plane in which a pupil plane field distribution is formed is labeled 32. An image plane in which an image of the source (e.g. the end of the optical fiber) is formed is labeled 34. An aperture plate 13 is provided in a pupil plane 32. The aperture plate 13 may take the form depicted by inset 13H for example (viewed from above). The aperture plate 13 imparts a desired pupil plane field distribution to the input radiation 34 provided to the beam splitter 48 and will be described in further detail below. The input radiation 34 is polarized by a polarizer 30 (e.g. linearly polarized).

As depicted in FIGS. 6-7, the optical unit 40 comprises a beam splitter 48. The beam splitter 48 splits the input radiation beam 34 into a first radiation beam and a second radiation beam. The optical unit 40 is part of an optical system (depicted in FIG. 5) that directs the first radiation beam and the second radiation beam onto a substrate W and directs reflected radiation from the substrate W onto a detector 38 (e.g. a CCD or CMOS sensor) via the beam splitter 48. In the embodiment shown the detector 38 is positioned in a pupil plane. The detector 38 records an intensity in a pupil plane field distribution of a combination of the first radiation beam and the second radiation beam after reflection from the substrate W. As will be described in further detail below, the detector 38 detects radiation resulting from interference between the first radiation beam and the second radiation beam. In an embodiment the interference is such that the first radiation beam and the second radiation beam interfere more destructively (e.g. completely destructively) at the detector 38 for reflections from a symmetric component of a target structure than for reflections from an asymmetric component of the target structure. A background signal that does not contain information about asymmetry in a target structure is thereby removed or reduced. A portion of the signal that does contain information about the asymmetry in the target structure is retained. The sensitivity with which the asymmetry can be measured is thereby increased. The interference between the first radiation beam and the second radiation beam comprises interference between different points in a pupil plane field distribution. In these embodiments, pairs of points in the pupil plane field distribution that are to interfere with each other are arranged symmetrically about a common point (for point symmetry) or common axis (for mirror symmetry) of symmetry. When the pupil plane field distribution is perfectly symmetric about the common point or axis of symmetry the pairs of points have the same amplitude and can be made to interfere destructively by applying a 180 degrees phase shift between them. A symmetric background signal can thus be removed efficiently and any deviation from symmetry can be detected with high sensitivity. FIG. 6 described below depicts an example in which different points in the pupil plane field distribution are interfered mirror symmetrically. FIG. 7 described below depicts an example in which different points in the pupil plane field distribution are interfered point symmetrically.

In an embodiment, the reflected first radiation beam and the reflected second radiation beam reaching the detector result from zeroth order reflection from a target structure on the substrate W. The approach is therefore suitable for measuring high resolution features (e.g. features at the resolution of device structures to be manufactured).

In the embodiment of FIGS. 4-7 the optical system 60 is such that the first radiation beam and the second radiation beam propagate in opposite directions around a common optical path comprising a first branch 61 and a second branch 62. In the embodiment shown, the first branch 61 and the second branch 62 have optical elements in common (e.g. lenses 42A, 42B and 44) although the radiation propagates through different portions of these common optical elements in each branch. The common optical path is common in the sense that the optical trajectory of the first radiation beam and the optical trajectory of the second radiation beam can be superimposed onto each other (within engineering tolerances). The only difference between the optical trajectories of the first radiation beam and the second radiation beam in the common optical path is that the first radiation beam and second radiation beam travel in opposite directions. The common optical path is a closed optical path. The first radiation beam propagates from the beam splitter 48 to the substrate W along the first branch 61 (downwards in the example shown) and from the substrate W back to the beam splitter 48 along the second branch 62 (upwards in the example shown). The second radiation beam propagates from the beam splitter 48 to the substrate W along the second branch 62 (downwards in the example shown) and from the substrate W back to the beam splitter 48 along the first branch 61 (upwards in the figure). The first radiation beam and the second radiation beam are focused onto the same location on the substrate, forming an image on the substrate W (e.g. an image of the source 11). A phase shift is applied to the first radiation beam relative to the second radiation beam to increase destructive interference between the first radiation beam and the second radiation beam at the detector 38 (relative to the case where no phase shift is applied). In an embodiment the phase shift is applied uniformly to the whole of the cross-section of the first radiation beam relative to the whole of the cross-section of the second radiation beam. In one particular class of embodiments, the phase shift is equal to 180 degrees. The phase shift is such as to cause the component of the detected radiation intensity containing information about the parameter of interest (e.g. overlay) to be enhanced by interference relative to the one or more other components of the detected radiation intensity.

Due to the common optical path of the first radiation beam and the second radiation beam, if the target structure from which the first radiation beam and the second radiation beam is reflected is fully symmetric (e.g. point symmetric or mirror symmetric), complete destructive interference can be achieved at the detector 38 for all points in the pupil plane field distribution, in the case of an applied phase difference of 180 degrees. Any asymmetry in the target structure, due to overlay for example, will cause incomplete destructive interference. The incomplete destructive interference provides a signal at the detector 38 that can be used to obtain a measure of the asymmetry. The interferometry thus removes unwanted background signal and improves a sensitivity with which the asymmetry can be measured.

The extent to which background can be removed will depend on alignment accuracy of optical elements such as the beam splitter 48 and/or optical imperfections. Imperfect alignment will lead to fringes (due to reflected beams from the first radiation beam and the second radiation beam not lying exactly on top of each other or not propagating in exactly the same direction). Imperfect optics will lead to incomplete background suppression, for example if the beam splitter 48 does not provide exactly 50/50 beam splitting.

In the example of FIG. 5, the first radiation beam and the second radiation beam are both focused onto the substrate W by lenses 42A, 42B and 44. An image plane between lenses 42A and 42B is labeled 34. The substrate W is also positioned in an image plane. A pupil plane between lenses 42B and 44 is labelled 32. Reflected radiation from the first radiation beam and the second radiation beam is directed to the detector 38, after passing a second time through the beam splitter 48, via lenses 18A and 18B. In an embodiment, the input radiation beam 34 is polarized and the first radiation beam and the second radiation beam both pass through a polarizer 36 that is crossed with respect to the polarization of the input radiation after reflection from the substrate W and before detection by the detector 38. In the embodiment shown the polarization of the input radiation beam 34 is provided by polarizer 30 and the crossed polarization is provided by a polarizer 36 positioned between the lens 18B and the detector 38. The polarizer 36 is crossed relative to the polarizer 30. In an embodiment, the polarizer 36 comprises a polarizing beam splitter. Contributions to the reflected radiation from asymmetry in a target structure (e.g. overlay) are present in the crossed polarization component. Contributions to the reflected radiation that are not related to asymmetry should not normally be present in the crossed polarization component. The use of crossed polarizers therefore further suppresses background signal that does not contain information about asymmetry in the target structure. An image plane between lenses 18A and 18B is labeled 34. A pupil plane after lens 18B and adjacent to the detector 38 is labeled 32. As mentioned above, in this embodiment the detector measures an intensity in the pupil plane.

In an embodiment, the first radiation beam and the second radiation beam are directed onto the substrate W symmetrically. The symmetry may result in a pupil plane field distribution of the first radiation beam being mirror symmetric or point symmetric with respect to a pupil plane field distribution of the second radiation beam (which is in the same plane as the pupil plane field distribution of the first radiation beam) prior to reflection of the first radiation beam and the second radiation beam from the substrate W. The optical system performs at least one flip or rotation of the pupil plane field distribution of radiation propagating in the first branch or the second branch such that the image from the first radiation beam and the image from the second radiation beam are respectively formed by radiation having pupil plane field distributions that are mirror symmetric or point symmetric with respect to each other.

In the example of FIG. 6 the pupil plane field distribution of radiation propagating in the first branch is flipped (reflected) such that the image from the first radiation beam and the image from the second radiation beam are respectively formed by radiation having pupil plane field distributions that are mirror symmetric with respect to each other. In embodiments of this type an optical path length compensator 50 may be provided to compensate for the additional optical path length introduced by the flipping of the pupil plane field distribution. In the particular example of FIG. 6, the pupil plane is flipped by pupil plane field distribution modifying unit 46 in the first branch 61. The optical path length compensator 50 is then positioned in the second branch 62.

The pupil plane field distribution modification unit 46 may be implemented in various ways. In the configuration shown, any combination of optical elements that achieves the desired function of changing the direction of the radiation beam (from horizontal to down) and flipping the pupil plane field distribution may be used. The functionality can be implemented using two suitably oriented mirrors or a pentaprism for example.

The optical path length compensator 50 may be implemented in various ways. Any combination of optical elements that achieves the desired function of making the optical path length from beam splitter 48 to the target structure on the substrate W the same for the first radiation beam and the second radiation beam (by compensating for the detour through the pupil plane field distribution modification unit 46) may be used. This is necessary to ensure that the target structure is in the image plane and therefore in focus (allowing optimal measurement of the target structure). In the particular example of FIG. 6, the optical path length compensator 50 comprises four mirrors. The optical path length compensator 50 could alternatively be implemented using right angle prisms, or a combination of right angle prisms and mirrors. The optical path length compensator 50 can be fixed (e.g. perfectly matched to the pupil plane field distribution modification unit 46) or tunable in length (for flexibility). In principle, a plate of glass could be used (because of the high index of refraction).

FIG. 7 depicts an alternative implementation of symmetrically directing the first radiation beam and the second radiation beam onto the substrate W. In contrast to the embodiment of FIG. 6 in which mirror symmetry is achieved, the arrangement of FIG. 7 results in the pupil plane field distribution of the first radiation beam being point symmetric with respect to the pupil plane field distribution of the second radiation beam prior to reflection of the first radiation beam and the second radiation beam from the substrate W. In the example of FIG. 7 this is achieved by modifying the arrangement of FIG. 6 to add an additional flip (mirror reflection) in the second branch 62. In the example shown, the additional flip is implemented by a dove prism 80. In an alternative embodiment, the additional flip is implemented using a roof top Amici prism, for example in place of one of the mirrors of the optical path length compensator 50. Alternatively, the additional flip is provided in the first branch 61. Alternatively, the effect can be achieved by rotation of the pupil plane field distributions, for example by implementing −90 degrees rotation in one of the branches and a +90 degrees rotation in the other branch. Point symmetry is desirable because it corresponds to interfering light beams that have interacted with the target from opposite directions. This may not be necessary for aligned grating targets where the symmetry of the targets themselves means that mirror symmetry in the pupil plane field distributions may be adequate. When the overlay target is not aligned, however, or when it is desired to measure product features, it may be necessary to use an embodiment such as that of FIG. 7 to ensure that the pupil plane field distributions are point symmetric.

The beam splitter 48 can be implemented in various ways. In the example shown a plate beam splitter is used. In other embodiments, a cube beam splitter or a pellicle beam splitter is used. For maximum destructive interference a 50/50 beam splitter is preferable.

When measuring asymmetry only, such as overlay only, a phase shift of 180 degrees will normally be used. However, using another phase shift will mean incomplete suppression of the background signal. This may be beneficial where it is desired to obtain information from the background signal. Information about symmetrical properties of the target (e.g. critical dimension) may be obtained for example. In an embodiment, the metrology apparatus is configured so that the phase shift is selectively controllable. The level of background can therefore be tuned as desired or the measurement can be switched between a mode that is sensitive predominantly to asymmetric properties and a mode that is sensitive predominantly to symmetric properties. In an embodiment, the phase shift is arranged at least temporarily to be close to 180 degrees but not exactly 180 degrees (e.g. 180 degrees plus or minus a shift of 1 degree, optionally 2 degrees, optionally 5 degrees, optionally 10 degrees, optionally 20 degrees). Control of the phase shift may be implemented by suitable adaptation of the beam splitter 48 for example.

Alternatively or additionally, measurement of symmetric properties may be achieved by providing apparatus to selectively remove the beam splitter 48 or to selectively replace the beam splitter with a different component, such as a two sided mirror. Alternatively or additionally, the beam splitter 48 may be configured to have a beam splitting ratio other than 50/50 (which will result in incomplete destructive interference with respect to symmetric components of the target structure).

It is a general property of an interferometer that when one output has a phase difference of 180 degrees, the other output has a phase difference of 0 degrees. Thus, when symmetric components for example interfere destructively in one output they will interfere constructively in the output. Based on this principle, an additional detector 39 may be provided that receives radiation output from the beam splitter 48 in the direction back towards the source 11. When a phase shift of 180 degrees is applied in the output leading to the detector 39, a phase shift of 0 degrees will be applied in the output leading back towards the source 11. An example arrangement is depicted in FIG. 5. In this example a further beam splitter 49 is provided that receives radiation output from the beam splitter 48 in the direction back towards the source 11. The further beam splitter 49 directs the radiation towards the detector 39 via lenses 18C and 18D. The detector 39 may be positioned in the image plane or pupil plane. Embodiments of this type allow simultaneous determination of the parameter of interest (e.g. overlay), via detector 38, and determination of further information from the background signal (e.g. critical dimension), via detector 39. The additional detector 39 may be provided regardless of the particular implementation details of the optical unit 40. In embodiments, the additional detector 39 is provided, optionally as depicted in FIG. 5, in combination with the optical unit 40 as described with reference to any of FIGS. 6, 7 and 10.

In the embodiments of FIGS. 6 and 7, a phase shift of 180 degrees between the reflected first radiation beam and the reflected second radiation beam is provided by the different ways the two beams are reflected or transmitted through the beam splitter. In the particular example shown the first radiation beam is output by reflection from one side (the left side) of the beam splitter 48 and is directed to the detector 38, after propagation around the common optical path, by reflection from the opposite side (the right side) of the beam splitter 48. This involves two reflections (one internal and one external). The second radiation beam, in contrast, is output by transmission through the beam splitter 48 and is directed to the detector 38, after propagation around the common optical path, by transmission through the beam splitter 48 a second time. Thus, if the optical path lengths are the same, the 180 degree phase shift introduced by the one external reflection from beam splitter provides the desired 180 degrees phase shift between the two radiation beams.

In an embodiment, the input radiation 34 to the beam splitter 48 comprises a pupil plane field distribution in which a first region of the pupil plane field distribution has been removed to leave only a second region of the pupil plane field distribution. In the embodiment of FIGS. 4-7 the first region is removed by aperture plate 13H. In an embodiment, the first region and the second region are oppositely oriented semicircles. This approach is desirable because it allows a maximum proportion of the radiation to contribute to the symmetrical illumination of the substrate W. A full circular pupil plane field distribution is provided at lens 44. One half is provided by the first radiation beam and the other half is provided by the second radiation beam. In an embodiment of this type, the flipping of the pupil plane field distribution may comprise a reflection about the straight edge of the semicircle of the first region of the pupil plane (FIG. 6) and/or a reflection about a line of mirror symmetry of the semicircle of the first region of the pupil plane (FIG. 7).

FIG. 6 depicts the pupil plane field distributions at various points in the optical path between the input of the input radiation 34 to the optical unit 40 and the output from the optical unit 40 of the radiation beams after reflection from the substrate W. The pupil plane field distribution of the input radiation 34 at the point of entry into the optical unit 40 is labelled 70 (as viewed from above). The arrow indicates the direction of propagation of the radiation (downwards in this case). The circle, square and triangle are provided in the figure (they are not present in the actual pupil plane field distributions) to identify reference parts of the pupil plane field distribution in order to facilitate visual tracking of the orientation of the pupil plane field distribution through the optical system in the figure.

As described above, the input radiation 34 is split by the beam splitter into a first radiation beam and a second radiation beam.

The first radiation beam follows the first branch 61 and passes through the pupil plane field distribution modification unit 46 before exiting the optical unit 40 downwards. The pupil plane field distribution at this stage (as viewed from above) is labelled 71A. As can be seen, pupil plane field distribution 71A is a mirror image of pupil plane field distribution 70. The axis of mirror symmetry is the straight edge of the semicircle. The first radiation beam passes through optics between the optical unit 40 and the substrate W (the rest of the first branch 61) to form an image on the substrate W. The first radiation beam is then reflected from the substrate W and propagates upwards along the second branch 62. The reflected first radiation beam passes through the optics between the substrate W and the optical unit 40. The pupil plane field distribution of the reflected first radiation beam on entry to the optical unit is labelled 71B (viewed from above). The optics between the optical unit 40 and the substrate W leads to rearrangement of the pupil plane field distribution 71A in a point symmetric way to provide the pupil plane field distribution 71B. The reflected first radiation beam passes through the optical path length compensator 50 upwards and is output from the optical unit 40 after reflection from the beam splitter 48. The pupil plane field distribution at this stage (viewed horizontally from the left) is labeled 71C.

The second radiation beam propagates around the common optical path in the opposite sense to the first radiation beam. The pupil plane field distribution of the second radiation beam after transmission through the beam splitter 48 and propagation through the optical path length compensator 50 is labelled 72A (viewed from above). Pupil plane field distribution 72A is identical to pupil plane field distribution 70. The second radiation beam passes through optics between the optical unit 40 and the substrate W (the rest of the second branch 62) to form an image on the substrate W. The second radiation beam is then reflected from the substrate W and propagates upwards along the first branch 61. The reflected second radiation beam passes through the optics between the substrate W and the optical unit 40. The pupil plane field distribution of the reflected second radiation beam on entry to the optical unit 40 is labelled 72B (viewed from above). The optics between the optical unit 40 and the substrate W leads to rearrangement of the pupil plane field distribution 72A in a point symmetric way to provide the pupil plane field distribution 72B. The reflected second radiation beam passes through the pupil plane field distribution modification unit 46 and is output from the optical unit 40 after transmission through the beam splitter 48 a second time. The pupil plane field distribution at this stage (viewed horizontally from the left) is labeled 72C.

FIG. 7 depicts the pupil plane field distribution at the same points as FIG. 6. The additional flip discussed above causes the pupil plane field distribution 71A to be point symmetric with respect to the pupil plane field distribution 72A instead of mirror symmetric.

Pupil plane field distributions 71C and 72C have the same orientation and lie exactly over each other (within engineering tolerances). This causes radiation originating from pairs of points that are mirror symmetric or point symmetric with respect to each other in the pupil plane field distribution defined by the combination of 71B and 72B in FIGS. 6 and 7 to interfere. Corresponding radiation intensities can then be detected at the detector 38. In the schematic illustrations of 6 and 7, the two triangles of 71B and 72B will interfere, the two squares of 71B and 72B will interfere, and the two circles of 71B and 72B will interfere. If the pupil plane field distributions 71B and 72B are exactly the same as each other (because the target structure has not induced any asymmetry), destructive interference will cause the whole pupil plane field distribution to be dark. Because two copies of the half pupil are spatially overlapped it is not necessary to have spatial coherence throughout the pupil. As discussed above, any asymmetry in the pupil plane field distribution will cause incomplete destructive interference and thereby provide bright regions. The bright regions can be detected by the detector 38 and provide information about asymmetry in the target structure.

The intensity recorded by the detector 38 is expected to have an approximately quadratic dependence on the asymmetry (e.g. overlay) in the target. Such dependence is depicted schematically in FIG. 8. This has two undesirable consequences. Firstly, the sensitivity of the measurement is relatively low because of the relatively flat scope of the quadratic curve near the origin. For a given size of overlay (indicated by half the width of the hatched rectangle in FIG. 8), the change in intensity 52 is relatively small (indicated by the height of the hatched rectangle, labeled 52). Secondly, the sense of the asymmetry (e.g. the direction of displacement of a pattern in one layer relative to a pattern in an overlying layer in the case of overlay) is not known due to the symmetry of the quadratic curve.

Figure 9:
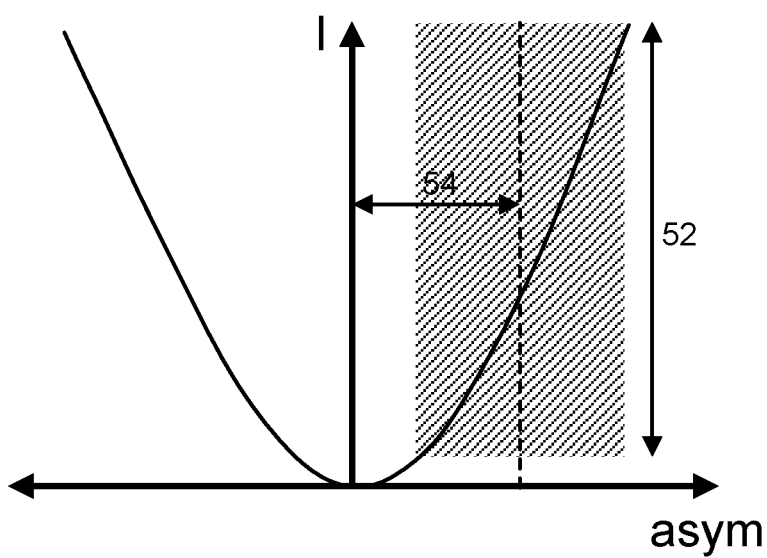
FIG. 9 is a graph depicting a variation of signal intensity I with target asymmetry for a biased target.

According to an embodiment, the above consequences are addressed by applying a known bias to the asymmetry (e.g. a bias to the overlay). Typically the bias will be larger than the asymmetry that it is desired to measure. The effect of such a bias is depicted in FIG. 9. The applied bias is indicated by arrow 54. Changes in intensity due to the asymmetry to be measured are much larger for the same amount of asymmetry in comparison with FIG. 8 (compare arrow 52 of FIG. 8 with arrow 52 of FIG. 9). Additionally, the sense of the asymmetry can be derived. Instead of a negative asymmetry produce the same change in intensity as a positive asymmetry (as in FIG. 8), in the arrangement of FIG. 9 a negative asymmetry leads to a large reduction in intensity and a positive asymmetry leads to a large increase in intensity. It is therefore possible to measure asymmetry with higher sensitivity and deduce the sense of the asymmetry.

In an alternative embodiment, a metrology apparatus is provided which uses an optical pupil symmetrization (OPS) system to provide the destructive interference for the reflections from symmetric components of the target structure and the constructive interference for the reflections from asymmetric components of the target structure (such as overlay). Details of how to implement an OPS system are provided in WO 2016/096310 A1, which is hereby incorporated in its entirety by reference.

Figure 10:
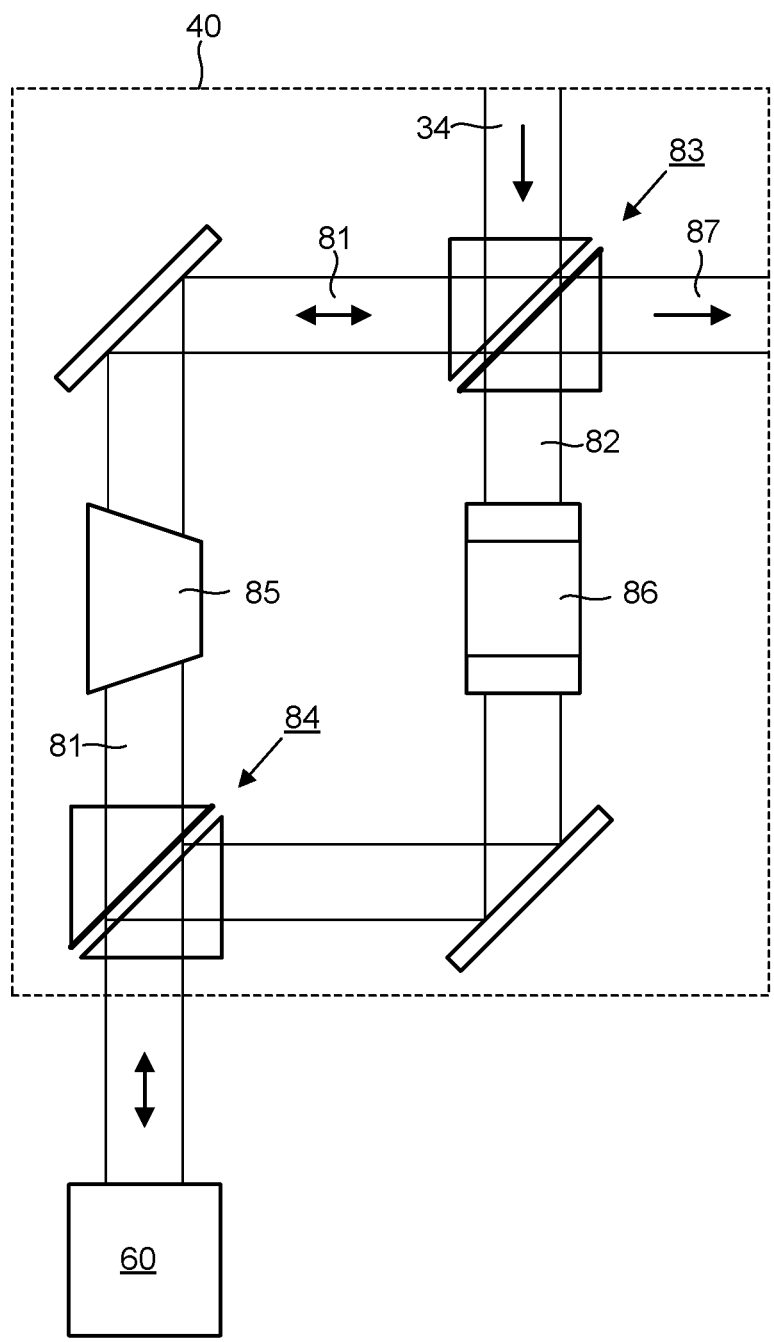
FIG. 10 depicts an alternative optical unit in which radiation passes through first and second beam splitters before and after reflection from the target structure.

In an embodiment, a metrology apparatus as described above with reference to FIGS. 4-9 is provided, except that the configuration of FIG. 4 may not comprise the aperture plate 13H to remove the first region of the pupil field distribution and the optical unit 40 is configured as shown in FIG. 10. The optical unit 40 of FIG. 10 comprises an OPS system. The optical unit 40 comprises a first beam splitter 83 that splits the radiation beam 34 into a first radiation beam and a second radiation beam. The optical unit 40 further comprises a second beam splitter 84 that recombines the first radiation beam and the second radiation beam. The first radiation beam propagates along a first optical branch 81 between the first beam splitter 83 and the second beam splitter 84. The second radiation beam propagates along a second optical branch 82 between the first beam splitter 83 and the second beam splitter 84. The first optical branch 81 and the second optical branch 82 flip or rotate a field distribution of the first radiation beam relative to a field distribution of the second radiation beam about two orthogonal axes. In the example of FIG. 10, the first radiation beam is flipped about a first axis in the first branch 81 using a first dove prism 85. The second radiation beam is flipped about a second axis, perpendicular to the first axis, in the second branch 82 using a second dove prism 86. In an alternative implementation, optical elements are provided that rotate the first radiation beam by −90 degrees in the first branch and rotate the second radiation beam by +90 degrees in the second branch. The optical path length along the first optical branch 81 is equal to the optical path length along the second optical branch 82.

The radiation beam passes through the first beam splitter 83 and the second beam splitter 84 before being reflected from the target structure (via optical system 60, which may be configured for example as shown in FIG. 5). The pupil plane field distribution of the radiation beam that is focused onto the structure is point symmetric. The radiation beam then additionally passes through the first beam splitter 83 and the second beam splitter 84 after reflection from the target structure (in the opposite direction). This results in a first output 87 from the first beam splitter 83 being formed by the first radiation beam and the second radiation beam interfering destructively for reflections from a symmetric component of the target structure and interfering constructively for reflections from an asymmetric component of the target structure. The first output 87 is therefore such that a component of the detected radiation intensity containing information about the parameter of interest (e.g. overlay) is enhanced relative to one or more other components (e.g. symmetric components).

Figure 21:
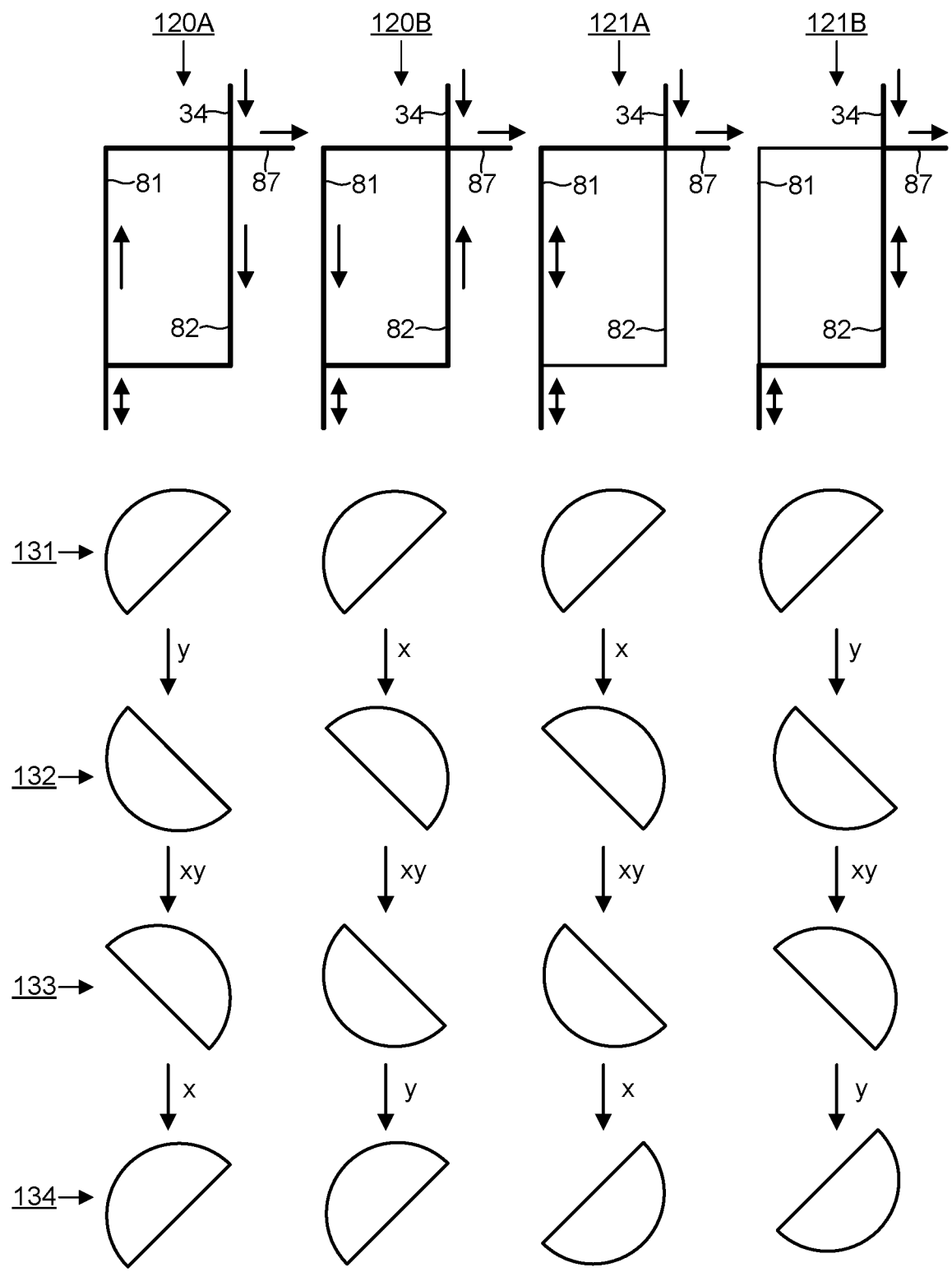
FIG. 21 depicts different propagation routes for radiation through an OPS system.

Radiation can propagate through the OPS system of FIG. 10 via four different routes, as depicted schematically in FIG. 21: 1) to the target structure via the second optical branch 82 and back to the first beam splitter 83 via the first optical branch 81 (corresponding to column 120A in FIG. 21), 2) to the target structure via the first optical branch 81 and back to the first beam splitter 83 via the second optical branch 82 (corresponding to column 120B in FIG. 21), 3) to the target structure via the first optical branch 81 and back to the first beam splitter 83 via the first optical branch 82 (corresponding to column 121A in FIGS. 21), and 4) to the target structure via the second optical branch 82 and back to the first beam splitter 83 via the second optical branch 82 (corresponding to column 121B in FIG. 21). Routes 1 and 2 (120A and 120B) considered together are similar to the common path interferometric embodiments discussed with reference to FIGS. 4-9. Routes 3 and 4 (121A and 121B) considered together resemble a double Mach Zehnder interferometer. Both pairs of routes provide a phase difference of 180 degrees in respect of reflection from symmetric components of the target structure, thereby leading to destructive interference. Asymmetric components may interfere constructively and thereby contribute to the detected signal via the first output 87.

Routes 3 and 4 (121A and 121B) do not have the common path advantage of Routes 1 and 2 (120A and 120B) and will be more sensitive to errors in alignment. It is therefore desirable to be able to separate the contribution from Routes 1 and 2 from the contribution from Routes 3 and 4.

In an embodiment, the separation is achieved by arranging for the radiation beam 34 input to the first beam splitter 83 to comprise a pupil plane field distribution in which a first region of the pupil plane field distribution has been removed to leave only a second region of the pupil plane field distribution. As described above with reference to FIGS. 4-7, this may be achieved for example via an aperture plate 13H in an upstream pupil plane. In an embodiment, the first region and the second region are oppositely oriented semicircles. In an embodiment, the detector 38 is configured to detect radiation from a first portion of a pupil plane field distribution of the first output 87 (e.g. a semicircular region) independently of radiation from a second portion of a pupil plane field distribution of the first output 87 (e.g. a different semicircular region). By arranging for the contribution from Routes 1 and 2 (120A and 120B) to be exclusively within the first portion of the pupil plane field distribution of the first output 87 and for the contribution from Routes 3 and 4 (121A and 121B) to be exclusively within the second portion of the pupil plane field distribution of the first output 87, it is possible to detect the contribution from Routes 1 and 2 (120A and 120B) independently of the contribution from Routes 3 and 4 (121A and 121B).

This approach is depicted schematically in FIG. 21 for the case where the radiation beam 34 input to the first beam splitter 83 comprises a semicircular pupil plane field distribution. Each column 120A, 120B, 121A, 121B corresponds to a different route for the radiation beam 34 through the first beam splitter 83 and the second beam splitter 84 to the target structure and back through the second beam splitter 84 and first beam splitter 83 to form the first output 87.

Row 131 represents an example orientation of the pupil plane field distribution (viewed along the beam direction) of the radiation beam 34 as input to the first beam splitter 83.

Row 132 represents the orientation of the pupil plane field distribution after a flipping operation in the first optical branch 81 or the second optical branch 82 (depending on the route taken by the radiation). Row 132 thus represents the orientation of the pupil plane field distribution prior to incidence of the radiation onto the target structure. The arrow between row 131 and row 132 indicates the nature of the flipping operation. "x" represents flipping in the x direction. "y" represents flipping in the y direction (perpendicular to x).

Row 133 represents the orientation of the pupil plane field distribution after flipping about x and y due to passing of the radiation through the objective lens to the target structure and back through the objective lens after reflection from the target structure. Row 133 thus represents the orientation of the pupil plane field distribution after reflection from the target structure. The arrow between row 132 and row 133 indicates the nature of the flipping operation. "xy" represents flipping about the x direction and about the y direction.

Row 134 represents the orientation of the pupil plane field distribution after a flipping operation in the first optical branch 81 or the second optical branch 82 (depending on the route taken by the radiation) after reflection from the target structure. Row 134 thus represents a final orientation of the pupil plane field distribution in the first output 87. The arrow between row 133 and row 134 indicates the nature of the flipping operation.

Row 134 shows that the orientation of the pupil plane field distribution is the same in the first output 87 for Routes 1 and 2 (120A and 120B). The orientation is the same as the orientation in the radiation beam 34 input to the first beam splitter 83. Thus, in this example the upper left portion of the pupil plane field distribution corresponds to the first portion of the pupil plane field distribution of the first output 87. The first portion of the pupil plane field distribution of the first output 87 is thus formed exclusively from: 1) radiation that has propagated to the target structure through the first optical branch 81 and back from the target structure through the second optical branch 82 (Route 2, 120B); and 2) radiation that has propagated to the target structure through the second optical branch 82 and back from the target structure through the first optical branch 81 (Route 1, 120A).

The orientation of the pupil plane field distribution is also the same in the first output 87 for Routes 3 and 4 (121A and 121B), and different from Routes 1 and 2 (120A and 120B). The orientation is flipped in the x direction and in the y direction relative to the orientation in the radiation beam 34 input to the first beam splitter 83. Thus, in this example the lower right portion of the pupil plane field distribution corresponds to the second portion of the pupil plane field distribution of the first output 87. The second portion of the pupil plane field distribution is formed exclusively from 1) radiation that has propagated to the target structure through the first optical branch 81 and back from the target structure through the first optical branch 81 (Route 3, 121A); and 2) radiation that has propagated to the target structure through the second optical branch 82 and back from the target structure through the second optical branch 82 (Route 4, 121B).

The separation of the radiation from Routes 1 and 2 into a different portion of the pupil plane field distribution relative to the radiation from Routes 3 and 4 allows the contribution from Routes 1 and 2 to be detected independently of the contribution from Routes 3 and 4.

The contribution from Routes 3 and 4, corresponding to the double Mach Zehnder interferometer, will be very sensitive to alignment errors, path length errors, and imperfections in optics. These errors can lead to fringes on the target structure, as well as in the first output 87. In an embodiment, these fringes are reduced or eliminated by arranging for the optical path length along the first optical branch 81 to be different from the optical path length along the second optical branch 82. In an embodiment, the difference is larger than a temporal coherence length of the radiation beam 34 input to the first beam splitter 83 (i.e. such that fringes on the target structure are substantially reduced or eliminated) but smaller than a depth of focus in a pupil plane 32 of the objective optical system (see FIG. 5). The approach thus improves the smoothness (homogeneity) of the illumination of the target structure. The contribution from Routes 3 and 4 will no longer interfere perfectly destructively in the first output 87. The second portion of the pupil plane field distribution, corresponding to the contribution from Routes 3 and 4, will instead comprise both symmetric and asymmetric contributions. However, the contribution from Routes 1 and 2 will still interfere destructively because both routes include propagation once along the shorter optical branch (81 or 82) and once along the longer optical branch (82 or 81), such that the total path length will be equal for each route. Due to the common path geometry of Routes 1 and 2, the interference will be less sensitive to alignment and optical imperfections, and will therefore provide highly sensitive access to the asymmetric contribution to the radiation.

Figure 11:
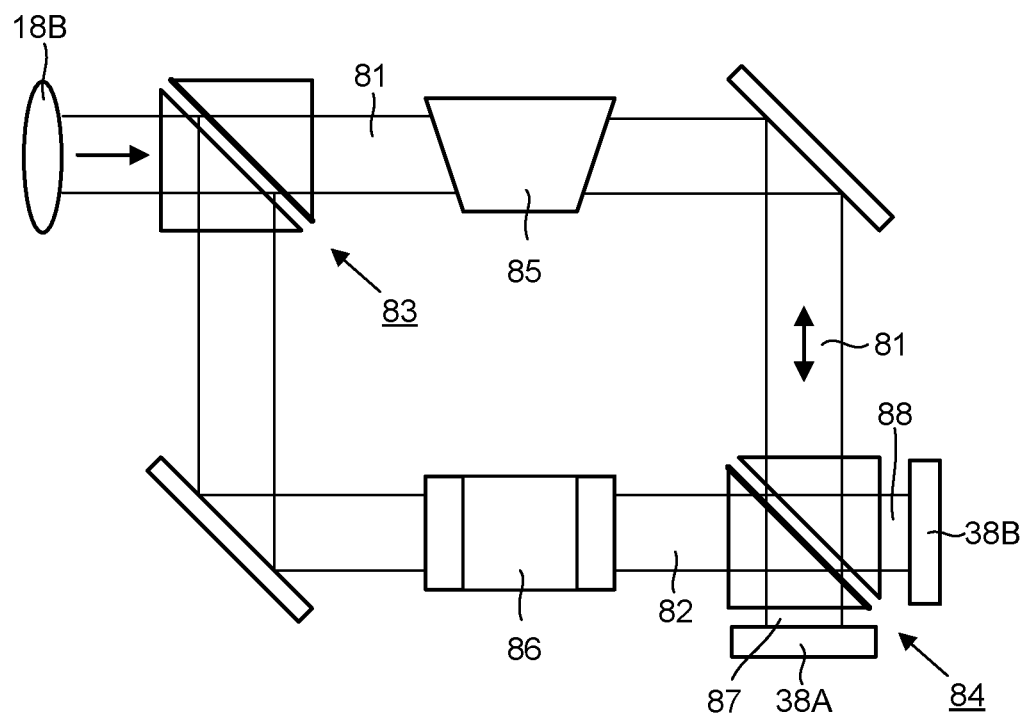
FIG. 11 depicts an optical arrangement in which radiation passes through first and second beam splitters only after reflection from the target structure.

FIG. 11 depicts an alternative embodiment in which the OPS system of FIG. 10 is positioned so that the radiation beam passes through only after reflection from the target structure (and not before). In embodiments of this type other arrangements may be provided to introduce spatial coherence in radiation incident on the structure and/or the source 11 may be configured to output spatially coherent radiation. The metrology apparatus in this case may be as described above with reference to FIGS. 4-9, except that the configuration of FIG. 4 may not comprise the aperture plate 13H to remove the first region of the pupil field distribution, the optical unit 40 in FIG. 10 consists of a single beam splitter, and the OPS system of FIG. 10 is provided after the lens 18B shown in FIG. 5. In this embodiment, a first detector 38A detects radiation output from a first output 87 of the second beam splitter 84. A second detector 38B detects radiation output from a second output 88 of the second beam splitter 84. The OPS system in this case operates according to the principles of a Mach Zehnder interferometer. When the path lengths are equal in the first optical branch 81 and the second optical branch 82 the first output 87 will be dark due to destructive interference and the second output 88 will be bright due to constructive interference. As in the embodiment of FIG. 10, dove prisms 85 and 86 flip the field distributions of the first radiation beam and the second radiation so that the two copies of the pupil are point symmetric when they are interfered. In the first detector 38A, the light is interfered destructively and only the asymmetry signal (from reflection from asymmetric components of the target structure) remains. This causes a component of the detected radiation intensity containing information about a parameter of interest (e.g. overlay) to be enhanced relative to other components. In the second detector 38B, the light is interfered constructively. This allows the second detector 38B to detect a radiation intensity in which the component containing information about a parameter of interest (e.g. overlay) is suppressed relative to other components. The second detector 38B can thus be used to measure the symmetric part of the pupil for example.

The above embodiments may be particularly usefully applied to measuring asymmetry in a target structure comprising a layered structure having a first component in a first layer and a second component in a second layer, in the case where a separation between the first layer and the second layer is greater than $\lambda/20$, where $\lambda$ is a wavelength of the input radiation beam. This may be the case for example where the method is applied to a structure after a lithographic development step but prior to a subsequent etching step. The increased sensitivity to asymmetry means that asymmetry (e.g. overlay between the first component and the second component) can be measured for high resolution structures even in cases such as these where the contribution to zeroth order reflection is expected to be extremely small (due to the large separation between the layers). Additionally or alternatively, measurement times can be reduced significantly.

Figure 12:
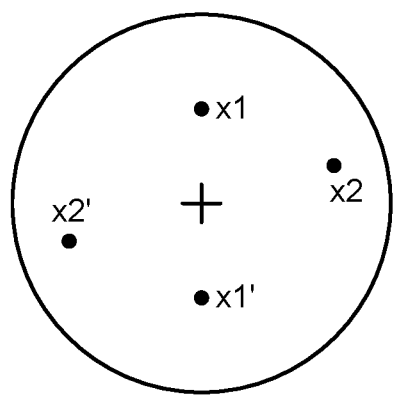
FIG. 12 depicts example point symmetric pairs of interfering points in a pupil plane distribution.
Figure 13:
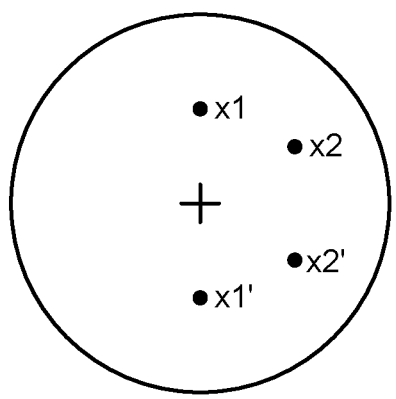
FIG. 13 depicts example mirror symmetric pairs of interfering points in a pupil plane field distribution.

The embodiments discussed above with reference to FIGS. 4-11 involve detecting a plurality of radiation intensities resulting from interference between radiation from a corresponding plurality of pairs of points in a pupil plane field distribution. In the example of FIG. 6, each pair of points are positioned mirror symmetrically with respect to each other about the same line of mirror symmetry. In the examples of FIGS. 7, 10 and 11, each pair of points are positioned point symmetrically with respect to each other about the same symmetry point. FIGS. 12 and 13 each depict two example pairs of points, labelled respectively x1 and x1', and x2 and x2'. In the example of FIG. 12, the pairs of points are point symmetric (about the center of the circular pupil plane field distribution). In the example of FIG. 13, the pairs of points are mirror symmetric (about an axis of mirror symmetry lying along the diameter of the circular pupil plane field distribution). In a case where a phase difference of 180 degrees is applied between radiation originated from the two points of each pair, detected intensities will be given as follows:

$$I(1)=|E(x1)-E(x1')|^2$$

$$I(2)=|E(x2)-E(x2')|^2$$

where E(x1), E(x1'), E(x2), and E(x2') represent the amplitude and phases of the radiation at the respective points x1, x1', x2, and x2'.

In an embodiment, an optical weighting unit is provided that modifies either or both of the phase and amplitude of radiation from one or more different points in the pupil plane field distribution prior to radiation from those points contributing to the detected radiation intensity. In an embodiment, the optical weighting unit comprises a reference optical target or a programmable spatial light modulator. In an embodiment, the optical weighting unit may be implemented as part of a grating for splitting a radiation beam into a plurality of radiation beams, as described below with reference to FIG. 15. The optical weighting unit makes it possible to fine tune the interference process, for example to correct for asymmetries in the target that are not associated with overlay (where overlay is being measured) or asymmetries in the optics. The weightings may be tuned for example to match the combined asymmetry from all factors other than overlay. If overlay is zero complete destructive interference will be achieved even in the presence of other asymmetries. Non-zero overlay can then be measured with greater sensitivity. The optical weightings result in the detected intensities for the examples of FIGS. 12 and 13 being given as follows:

$$I(1)=|E_{ref}(x1)E(x1)-E_{ref}(x1')E(x1')|^2$$

$$I(2)=|E_{ref}(x2)E(x2)-E_{ref}(x2')E(x2')|^2$$

where $E_{ref}(x1)$, $E_{ref}(x1')$, $E_{ref}(x2)$, and $E_{ref}(x2')$ represent the weightings applied at the respective points x1, x1', x2, and x2'.

Figure 14:
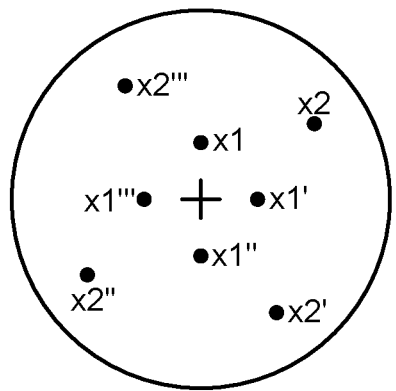
FIG. 14 depicts example groups of four interfering points in a pupil plane field distribution.

The interference between plural different points in the pupil plane field distribution can comprise more than two points in each case. FIG. 14 depicts example groups of four interfering points in a pupil plane field distribution. This may be achieved by overlapping four pupil plane field distributions that have been rotated by 90 degrees with respect to each other (e.g. by using additional beamsplitters to make more copies and recombine them). The detected intensities in this case would be as follows (with weightings applied to each point):

$$I(1)=|E_{ref}(x1)E(x1)+E_{ref}(x1')E(x1')+E_{ref}(x1'')E(x1'')+E_{ref}(x1''')E(x1''')|^2$$

$$I(2)=|E_{ref}(x2)E(x2)+E_{ref}(x2')E(x2')+E_{ref}(x2'')E(x2'')+E_{ref}(x2''')E(x2''')|^2$$

Figure 15:
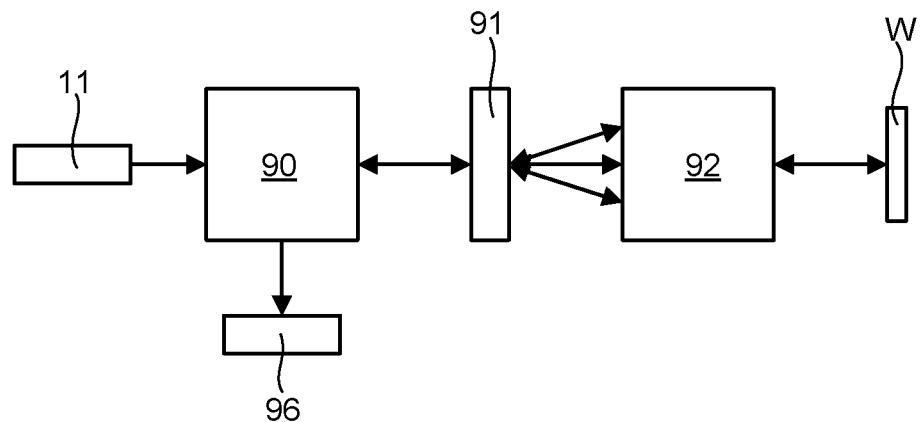
FIG. 15 depicts a metrology apparatus configured to interfere radiation from groups of three points in a pupil plane field distribution.
Figure 16:
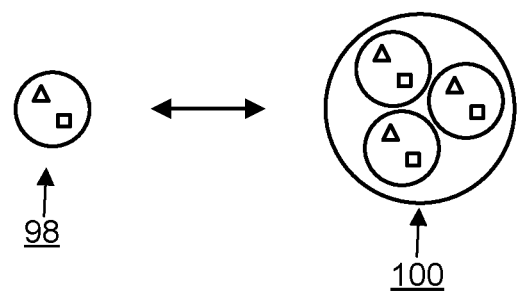
FIG. 16 depicts a first pupil plane field distribution (left) and a second pupil plane field distribution (right) formed from multiple copies of the first pupil plane field distribution in the metrology apparatus of FIG. 15.

FIGS. 15 and 16 depict an embodiment in which groups of three points are interfered. FIG. 15 depicts the metrology apparatus schematically. The metrology apparatus comprises an optical system 90-92 that focuses radiation from an incoherent source 11 onto a structure on a substrate W and directs reflected radiation from the structure onto a detector 96. The detector 96 detects a radiation intensity resulting from interference between radiation from groups of three different points in a pupil plane field distribution. The interference is such that a component of the detected radiation intensity containing information about the parameter of interest is enhanced relative to one or more other components of the detected radiation intensity. The optical system splits the radiation beam into three radiation beams and later recombines the three radiation beams to provide the interference between the groups of different points. In the embodiment shown the splitting and recombination are achieved by a spatial light modulator 91 programmed to emulate three overlapping diffraction gratings that are rotated relative to each other (e.g. by 120 degrees). In other embodiments an optical element is fabricated to achieve this functionality. In still other embodiments, beam splitters are used. In the embodiment shown, the splitting is achieved as radiation propagates from left to right in FIG. 15 through the spatial light modulator 91. The recombination is achieved as radiation propagates from right to left in FIG. 15 through the spatial light modulator 91 (after reflection from the structure on the substrate W). The spatial light modulator 91 creates multiple copies of a first pupil plane field distribution 98 (depicted schematically in FIG. 16 on the left). The first pupil plane field distribution is present to the left of the spatial light modulator 91 in the example of FIG. 15. The multiple copies of the first pupil plane field distribution 98 form a second pupil plane field distribution 100 (depicted schematically in FIG. 16 on the right). Radiation from the second pupil plane field distribution 100 is focused onto the structure on the substrate W by the element 92 of the optical system 90-92. The interference between the radiation from different points in the pupil plane field distribution comprises interference between radiation from different points in the second pupil plane field distribution 100 after reflection from the structure (i.e. between points corresponding to the triangles and, separately, between points corresponding to the squares). The principle of FIGS. 15 and 16 can be applied to arrangements in which the radiation beam is split into more than three radiation beams if it is desired to interfere radiation from groups comprising more than three points. In an embodiment, the spatial light modulator 91 can operate as an optical weighting unit as described above, by suitable programming of spatial light modulation (e.g. to modify the contrast and/or phase shifts provided by the gratings).

In an embodiment, the arrangement of FIGS. 15 and 16 is modified to provide a further spatial light modulator to provide additional freedom. In such an embodiment, the spatial light modulator 91 (or other beam splitting component) may be provided to the left of the optical system 90, between the optical system 90 and the source 11, and the further spatial light modulator is positioned between the optical system 90 and the detector 96.

The embodiments disclosed above extract an asymmetric signal from a symmetric background. FIGS. 17-20 disclose example embodiments in which a signal having a first symmetry is extracted from a background having a different symmetry.

Figure 17:
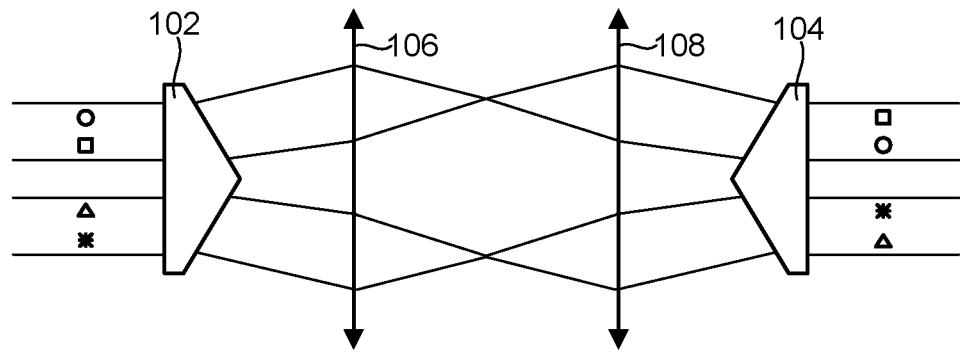
FIG. 17 depicts an optical arrangement for interferometrically extracting a mirror symmetric or point symmetric signal from a symmetric background.
Figure 18:
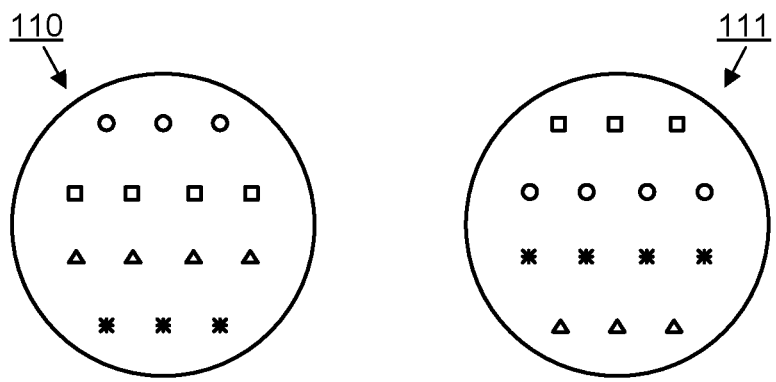
FIG. 18 depicts an example first pupil plane field distribution (left) on entry into the optical arrangement of FIG. 17 from the left and a second pupil plane field distribution (right) on exit from the optical arrangement of FIG. 17 to the right, in a case where the optical arrangement of FIG. 17 is configured to extract a mirror symmetric signal from a symmetric background.
Figure 19:
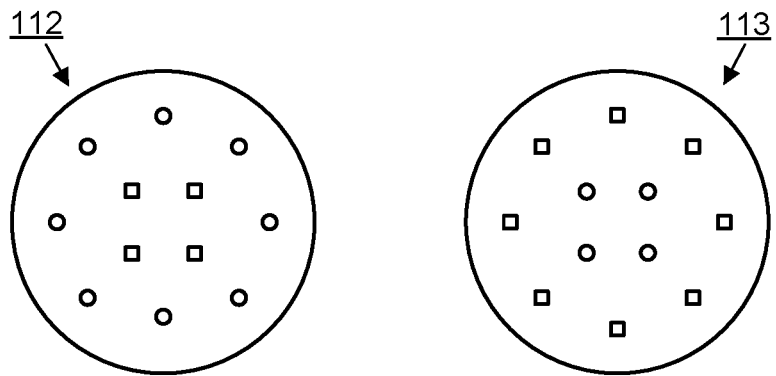
FIG. 19 depicts an example first pupil plane field distribution (left) on entry into the optical arrangement of FIG. 17 from the left and a second pupil plane field distribution (right) on exit from the optical arrangement of FIG. 17 to the right, in a case where the optical arrangement of FIG. 17 is configured to extract a point symmetric signal from a symmetric background.
Figure 20:
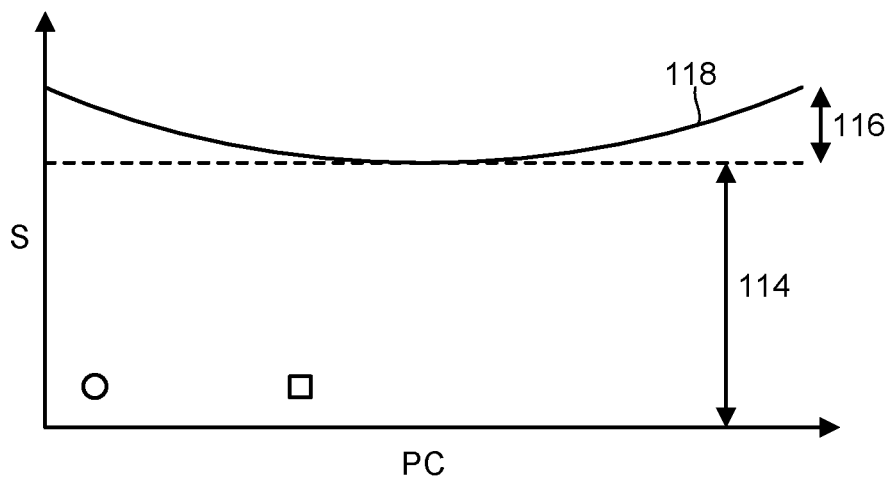
FIG. 20 is a graph schematically depicting a variation of a target response (intensity and phase) as a function of pupil position to illustrate the symmetric background and the point or mirror symmetric signal to be extracted.

FIG. 17 depicts an optical arrangement comprising refractive elements 102 and 104 and lenses 106 and 108 that together provide interference between different points arranged symmetrically about a point or about a line of mirror symmetry in a pupil plane field distribution. The optical arrangement could be used in the optical unit of FIG. 10, for example, as an alternative to the flips or rotations that provide the point symmetry. Radiation enters the optical arrangement from the left, passes through from left to right and then from right to left, and exits the optical arrangement to the left. The interference is such that points corresponding to the squares interfere with points corresponding to the circles and the points corresponding to the triangles interfere with points corresponding to the stars (as can be appreciated by following the example ray traces). It will be appreciated that the arrangement can provide mirror symmetric interference or point symmetric interference depending on the symmetry of the refractive elements 102 and 104. FIG. 18 depicts an example pupil plane field distribution 110 on the left of refractive element 102 and a pupil plane field distribution 111 on the right of refractive element 104 for the case where the refractive elements 102 and 104 are mirror symmetric. FIG. 19 depicts corresponding pupil plane field distributions 112 and 113 in the case where the refractive elements 102 and 104 are point symmetric about an optical axis of the optical arrangement. FIG. 20 is a graph showing schematically an example symmetric signal that could be extracted using such an arrangement. The horizontal axis represents a pupil coordinate (PC) from an edge of a pupil plane field distribution towards a center of a pupil plane field distribution. The vertical axis represents a signal level (S). The circle and square depict positions corresponding to the circle and square in the radiation entering the optical arrangement of FIG. 17 from the left. The signal of interest 116 is symmetric in the sense that it falls and rises symmetrically about a center line of the pupil plane field distribution (from left to right in FIG. 20) but is offset by a large symmetric background 114 (having a different symmetry). The interference provided by the arrangement of FIG. 17 allows this symmetric signal to be extracted from the background.

The concepts disclosed herein may find utility beyond post-lithography measurement of structures for monitoring purposes. For example, such a detector architecture may be used in future alignment sensor concepts that are based on pupil plane detection, used in lithographic apparatuses for aligning the substrate during the patterning process.

The targets described above may be metrology targets specifically designed and formed for the purposes of measurement. However, the ability to measure high resolution targets means the embodiments may also be applied to targets that are functional parts of devices formed on the substrate. Many devices have regular, grating-like structures. The terms 'target grating' and 'target' as used herein do not require that the structure has been provided specifically for the measurement being performed.

The metrology apparatus can be used in a lithographic system, such as the lithographic cell LC discussed above with reference to FIG. 2. The lithographic system comprises a lithographic apparatus LA that performs a lithographic process. The lithographic apparatus may be configured to use the result of a measurement by the metrology apparatus of a structure formed by the lithographic process when performing a subsequently lithographic process, for example to improve the subsequent lithographic process.

An embodiment may include a computer program containing one or more sequences of machine-readable instructions describing methods of measuring targets on a structures and/or analyzing measurements to obtain information about a lithographic process. There may also be provided a data storage medium (e.g., semiconductor memory, magnetic or optical disk) having such a computer program stored therein. Where an existing lithography or metrology apparatus is already in production and/or in use, the invention can be implemented by the provision of updated computer program products for causing a processor to perform the methods described herein.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic, and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Further embodiments according to the invention are described in below numbered clauses:

1. A metrology apparatus for measuring a structure formed on a substrate to determine a parameter of interest, the metrology apparatus comprising:

an optical system configured to focus radiation onto the structure and direct radiation after reflection from the structure onto a detector, wherein:

the optical system is configured such that the detector detects a radiation intensity resulting from interference between radiation from at least two different points in a pupil plane field distribution, wherein the interference is such that a component of the detected radiation intensity containing information about the parameter of interest is enhanced relative to one or more other components of the detected radiation intensity.

2. The apparatus of clause 1, wherein the optical system is configured to cause the detector to detect a plurality of radiation intensities resulting from interference between radiation from a corresponding plurality of pairs of points in a pupil plane field distribution, each pair of points being positioned mirror symmetrically with respect to each other about the same line of mirror symmetry.

3. The apparatus of clause 1, wherein the optical system is configured to cause the detector to detect a plurality of radiation intensities resulting from interference between radiation from a corresponding plurality of pairs of points in a pupil plane field distribution, each pair of points being positioned point symmetrically with respect to each other about the same symmetry point.

4. The apparatus of any of clauses 1-3, further comprising an optical weighting unit configured to modify either or both of the phase and amplitude of radiation from one or more different points in the pupil plane field distribution prior to radiation from those points contributing to the detected radiation intensity.

5. The apparatus of any preceding clause, wherein the optical system is configured to split a radiation beam into a plurality of radiation beams and later recombine the plurality of radiation beams in order to cause the interference between the radiation from different points in the pupil plane field distribution.

6. The apparatus of clause 5, wherein:

the splitting of the radiation beam into the plurality of radiation beams creates multiple copies of a first pupil plane field distribution;

the optical system forms a second pupil plane field distribution using the multiple copies of the first pupil field distribution;

radiation in the second pupil plane field distribution is focussed onto the structure; and the interference between the radiation from different points in the pupil plane field distribution comprises interference between radiation from different points in the second pupil plane field distribution after reflection from the structure.

7. The apparatus of any of clauses 1-4, wherein the optical system comprises a beam splitter configured to split a radiation beam into a first radiation beam and a second radiation beam, and the optical system is configured such that:

the first radiation beam and the second radiation beam propagate in opposite directions around a common optical path comprising a first branch and a second branch, the first radiation beam propagating from the beam splitter to the substrate along the first branch and from the substrate back to the beam splitter along the second branch, and the second radiation beam propagating from the beam splitter to the substrate along the second branch and from the substrate back to the beam splitter along the first branch; and a phase shift is applied to the first radiation beam relative to the second radiation beam, the phase shift being such as to cause the component of the detected radiation intensity containing information about the parameter of interest to be enhanced by interference relative to the one or more other components of the detected radiation intensity.

8. The apparatus of clause 7, wherein the phase shift is applied uniformly to the whole of the cross-section of the first radiation beam relative to the whole of the cross-section of the second radiation beam.

9. The apparatus of clause 7 or 8, wherein the phase shift is 180 degrees.

10. The apparatus of any of clauses 7-9, wherein the optical system is configured to perform at least one flip or rotation of the pupil plane field distribution of radiation propagating in the first branch or the second branch such that the image from the first radiation beam and the image from the second radiation beam are respectively formed by radiation having pupil plane field distributions that are mirror symmetric or point symmetric with respect to each other.

11. The apparatus of clause 10, further comprising an optical path length compensator in the first branch or the second branch to compensate for any additional optical path length introduced by the at least one flip or rotation of the pupil plane field distribution.

12. The apparatus of any of clauses 7-11, configured so that the radiation beam input to the beam splitter comprises a pupil plane field distribution in which a first region of the pupil plane field distribution has been removed to leave only a second region of the pupil plane field distribution.

13. The apparatus of clause 12, wherein the first region and the second region are oppositely oriented semicircles.

14. The apparatus of clause 13, wherein the at least one flip or rotation of the pupil plane field distribution comprises one or both of: a reflection about the straight edge of the semicircle of the first region of the pupil plane, and a reflection about a line of mirror symmetry of the semicircle of the first region of the pupil plane.

15. The apparatus of any of clauses 7-14, wherein the phase shift is at least partially provided by arranging for the first radiation beam to be output by reflection from one side of the beam splitter and to be directed to the detector after propagation around the common optical path by reflection from the opposite side of the beam splitter and for the second radiation beam to be output by transmission through the beam splitter and to be directed to the detector after propagation around the common optical path by transmission through the beam splitter.

16. The apparatus of any of clauses 7-15, wherein the first radiation beam and the second radiation beam are focused onto the same location on the substrate.

17. The apparatus of clause 16, wherein the first radiation beam and the second radiation beam form an image at the same location on the substrate.

18. The apparatus of clause 16 or 17, wherein a pupil plane field distribution of the first radiation beam to be focused onto the substrate is mirror symmetric with respect to a pupil plane field distribution of the second radiation beam to be focused onto the substrate.

19. The apparatus of any of clauses 16-18, wherein a pupil plane field distribution of the first radiation beam to be focused onto the substrate is point symmetric with respect to a pupil plane field distribution of the second radiation beam to be focused onto the substrate.

20. The apparatus of any of clauses 1-4, wherein the optical system comprises:

a first beam splitter configured to split a radiation beam into a first radiation beam and a second radiation beam; and a second beam splitter configured to recombine the first radiation beam and the second radiation beam, wherein the first radiation beam propagates along a first optical branch between the first beam splitter and the second beam splitter and the second radiation beam propagates along a second optical branch between the first beam splitter and the second beam splitter, and the first and second optical branches are configured such that at least a portion of the field distribution of the first radiation beam is flipped or rotated relative to a corresponding portion of the field distribution of the second radiation beam; and the detector is configured to detect radiation from a first output of either of the first beam splitter and the second beam splitter after reflection from the structure, wherein the first output is formed by the first radiation beam and the second radiation beam interfering in such a way that the component of the detected radiation intensity containing information about the parameter of interest is enhanced relative to the one or more other components of the detected radiation intensity.

21. The apparatus of clause 20, wherein the optical path length along the first optical branch is equal to the optical path length along the second optical branch.

22. The apparatus of clause 20, wherein the optical path length along the first optical branch is different from the optical path length along the second optical branch, the difference being larger than a temporal coherence length of the radiation beam input to the first beam splitter and smaller than a depth of focus in a pupil plane of the optical system.

23. The apparatus of any of clauses 20-22, wherein the optical system is configured such that the radiation beam passes through the first beam splitter and the second beam splitter before reflection from the structure.

24. The apparatus of clause 23, wherein the optical system is configured such that the radiation beam additionally passes through the first beam splitter and the second beam splitter after reflection from the structure, being split into the first radiation beam and the second radiation by the second beam splitter and recombined by the first beam splitter, the first radiation beam and the second radiation beam interfering at the first beam splitter such that said first output of the first beam splitter is formed by the first radiation beam and the second radiation beam interfering in such a way that the component of the detected radiation intensity containing information about the parameter of interest is enhanced relative to the one or more other components of the detected radiation intensity.

25. The apparatus of any of clauses 20-22, wherein the optical system is configured such that the radiation beam passes through the first beam splitter and the second beam splitter only after reflection from the structure.

26. The apparatus of any of clauses 20-25, comprising a further detector configured to detect radiation output from a second output from either of the first beam splitter and the second beam splitter, wherein the second output is formed by the first radiation beam and the second radiation beam interfering in such a way that the component of the detected radiation intensity containing information about the parameter of interest is suppressed relative to the one or more other components of the detected radiation intensity.

27. The apparatus of any of clauses 20-26, configured so that the radiation beam input to the first beam splitter comprises a pupil plane field distribution in which a first region of the pupil plane field distribution has been removed to leave only a second region of the pupil plane field distribution.

28. The apparatus of clause 27, wherein the first region and the second region are oppositely oriented semicircles.

29. The apparatus of clause 27 or 28, wherein the detector is configured to detect radiation from a first portion of a pupil plane field distribution of the first output independently of radiation from a second portion of a pupil plane field distribution of the first output.

30. The apparatus of clause 29, wherein:
the first portion of the pupil plane field distribution of the first output is formed exclusively from radiation that has propagated to the structure through the first optical branch and back from the structure through the second optical branch, and radiation that has propagated to the structure through the second optical branch and back from the structure through the first optical branch; and
the second portion of the pupil plane field distribution of the first output is formed exclusively from radiation that has propagated to the structure through the first optical branch and back from the structure through the first optical branch, and radiation that has propagated to the structure through the second optical branch and back from the structure through the second optical branch.

31. The apparatus of any preceding clause, configured such that the radiation focused onto the structure is polarized and the radiation passes through a polarizer that is crossed with respect to the polarization of the radiation focused onto the structure after reflection from the structure.

32. The apparatus of any preceding clause, wherein the parameter of interest is overlay between different layers of the structure.

33. A lithographic system comprising:
a lithographic apparatus configured to perform a lithographic process; and
the metrology apparatus of any preceding clause.

34. A method of measuring a structure formed on a substrate to determine a parameter of interest, the method comprising:
focusing radiation onto the structure and using a detector to detect radiation after reflection from the structure, wherein:
the detector detects a radiation intensity resulting from interference between radiation from at least two different points in a pupil plane field distribution, wherein the interference is such that a component of the detected radiation intensity containing information about the parameter of interest is enhanced relative to one or more other components of the detected radiation intensity.

35. The method of clause 34, wherein the structure comprises a layered structure having a first component in a first layer and a second component in a second layer, and the separation between the first layer and the second layer is greater than $\lambda/20$, where $\lambda$, is a wavelength of the input radiation beam.

36. The method of clause 34 or 35, wherein the method is applied to a structure after a lithographic development step but prior to a subsequent etching step.

37. The method of any of clauses 34-36, wherein the parameter of interest comprises an asymmetry in the structure.

38. The method of clause 37, wherein the parameter of interest comprises overlay between different layers in the structure.

39. The method of clause 37 or 38, wherein a known bias in the asymmetry of the structure is applied to the structure.

40. The method of any of clauses 34-39, wherein the detected radiation intensity results from zeroth order reflection from the structure.

The breadth and scope of the present invention should not be limited by any of the above-described exemplary embodiments, but should be defined only in accordance with the following claims and their equivalents.

The invention claimed is:

1. A metrology apparatus for measuring a structure formed on a substrate to determine a parameter of interest, the metrology apparatus comprising:
a first detector;
a second detector; and
an optical system configured to focus radiation onto the structure and to direct a first portion of radiation after reflection from the structure onto the first detector, and direct a second portion of radiation after reflection from the structure onto the second detector, wherein:
the optical system is configured such that the first detector detects a radiation intensity resulting from interference between radiation from at least two different points in a pupil plane field distribution,
the interference is such that a component of the detected radiation intensity containing information about the parameter of interest is enhanced relative to one or more other components of the detected radiation intensity, and
the second detector detects a parameter different from the radiation intensity.

2. The apparatus of claim 1, wherein the optical system is configured to cause the first detector to detect a plurality of radiation intensities resulting from interference between radiation from a corresponding plurality of pairs of points in a pupil plane field distribution, each pair of points being positioned mirror symmetrically with respect to each other about the same line of mirror symmetry.

3. The apparatus of claim 1, wherein the optical system is configured to cause the first detector to detect a plurality of radiation intensities resulting from interference between radiation from a corresponding plurality of pairs of points in a pupil plane field distribution, each pair of points being positioned point symmetrically with respect to each other about the same symmetry point.

4. The apparatus of claim 1, further comprising:
an optical weighting unit configured to modify either or both of phase and amplitude of radiation from one or more different points in the pupil plane field distribution prior to radiation from those points contributing to the detected radiation intensity by the first detector.

5. The apparatus of claim 1, wherein the optical system is configured to split a radiation beam into a plurality of radiation beams and later recombine the plurality of radiation beams in order to cause the interference between the radiation from different points in the pupil plane field distribution.

6. The apparatus of claim 5, wherein:
the splitting of the radiation beam into the plurality of radiation beams creates multiple copies of a first pupil plane field distribution;
the optical system forms a second pupil plane field distribution using the multiple copies of the first pupil field distribution;
radiation in the second pupil plane field distribution is focused onto the structure; and
the interference between the radiation from different points in the first pupil plane field distribution comprises interference between radiation from different points in the second pupil plane field distribution after reflection from the structure.

7. The apparatus of claim 1, wherein the optical system comprises:
a beam splitter configured to split a radiation beam into a first radiation beam and a second radiation beam, and the optical system is configured such that:
the first radiation beam and the second radiation beam propagate in opposite directions around a common optical path comprising a first branch and a second branch,
the first radiation beam propagating from the beam splitter to the substrate along the first branch and from the substrate back to the beam splitter along the second branch,
the second radiation beam propagating from the beam splitter to the substrate along the second branch and from the substrate back to the beam splitter along the first branch; and
a phase shift is applied to the first radiation beam relative to the second radiation beam, the phase shift being such as to cause the component of the detected radiation intensity containing information about the parameter of interest to be enhanced by interference relative to the one or more other components of the detected radiation intensity.

8. The apparatus of claim 7, wherein the phase shift is applied uniformly to a whole of a cross-section of the first radiation beam relative to a whole of a cross-section of the second radiation beam.

9. The apparatus of claim 7, wherein the phase shift is 180 degrees.

10. The apparatus of claim 7, wherein the optical system is configured to perform at least one flip or rotation of the pupil plane field distribution of radiation propagating in the first branch or the second branch such that the image from the first radiation beam and the image from the second radiation beam are respectively formed by radiation having pupil plane field distributions that are mirror symmetric or point symmetric with respect to each other.

11. The apparatus of claim 10, further comprising an optical path length compensator in the first branch or the second branch to compensate for any additional optical path length introduced by the at least one flip or rotation of the pupil plane field distribution.

12. The apparatus of claim 7, configured so that the radiation beam input to the beam splitter comprises a pupil plane field distribution in which a first region of the pupil plane field distribution has been removed to leave only a second region of the pupil plane field distribution.

13. The apparatus of claim 12, wherein the first region and the second region are oppositely oriented semicircles.

14. The apparatus of claim 13, wherein the optical system is configured to perform at least one flip or rotation of the pupil plane field distribution comprising one or both of: a reflection about the straight edge of the semicircle of the first region of the pupil plane, and a reflection about a line of mirror symmetry of the semicircle of the first region of the pupil plane.

15. The apparatus of claim 7, wherein the phase shift is at least partially provided by arranging for the first radiation beam to be output by reflection from one side of the beam splitter and to be directed to the first detector after propagation around the common optical path by reflection from the opposite side of the beam splitter and for the second radiation beam to be output by transmission through the beam splitter and to be directed to the first detector after propagation around the common optical path by transmission through the beam splitter.

* * * * *